United States Patent
Sung et al.

(10) Patent No.: US 7,255,855 B2
(45) Date of Patent: Aug. 14, 2007

(54) SURFACE EXPRESSION METHOD OF PEPTIDES P5 AND ANAL3 USING THE GENE ENCODING POLY-GAMMA-GLUTAMATE SYNTHETASE

(75) Inventors: Moon-Hee Sung, Daejeon (KR); Seung-Pyo Hong, Daejeon (KR); Jong-Su Lee, Gyeonggi-do (KR); Chang-Min Jung, Seoul (KR); Kyung-Soo Hahm, Seoul (KR); Dong-Gun Lee, Daejeon (KR); Yoon Kyung Park, Jeonnam (KR); Chul-Joong Kim, Daejeon (KR); Ha-Ryoung Poo, Daejeon (KR)

(73) Assignee: Bioleaders Corporation (KR)

( * ) Notice: Subject to any disclaimer, the term of this patent is extended or adjusted under 35 U.S.C. 154(b) by 201 days.

(21) Appl. No.: 10/789,164

(22) Filed: Feb. 27, 2004

(65) Prior Publication Data
US 2005/0191720 A1 Sep. 1, 2005

(51) Int. Cl.
*A01N 63/00* (2006.01)
*C12N 15/00* (2006.01)
*C12N 1/20* (2006.01)

(52) U.S. Cl. ............ 424/93.2; 435/320.1; 435/252.33; 435/252.3

(58) Field of Classification Search ............... None
See application file for complete search history.

(56) References Cited

FOREIGN PATENT DOCUMENTS

| KR | 10-2000-0078615 | 6/2002 |
| KR | 10-2001-0057837 | 3/2003 |
| WO | WO 03/014360 A1 | 2/2003 |

OTHER PUBLICATIONS

Boman et al., FEB Letts. vol. 259, (1): 103-106, 1989.*
Cintas, L.M. et al., "Enterocins L50A and L50B, Two Novel Bacteriocins from *Enterococcus faecium* L50, Are Related to Staphylococcal Hemolysins," Journal of Bacteriology, Apr. 1998, vol. 180, No. 8, 1988-1994.
Bevins, C.L. and Zasloff, M., "Peptides from Frog Skin," Annu. Rev. Biochem, 1990, 59:395-414.
Miyasaki, K.T. and Lehrer, R. I., "β-sheet Antibiotic Peptides as Potential Dental Therapeutics," International Journal of Antimicrobial Agents 9, 1998, 269-280.
Boman, H.G., "Antibacterial Peptides: Key Components Needed in Immunity," Cell, vol. 65, 205-207, Apr. 19, 1991.
Boman, H.G., "Peptide Antibiotics and Their Role in Innate Immunity," Annu. Rev. Immunol, 1995, 13:61-92.
Boman, H.G., et al., "Antibacterial and Antimalarial Properties Peptides that are Cecropin-melittin Hybrids," Federation of European Biochemical Societies, vol. 259, No. 1, 103-106, Dec. 1989.
Wade, D. et al., "Antibacterial Peptides Designed as Analogs or Hybrids of Cecropins and Melittin," Int. J. Peptide Protein Res. 40, 1992, 429-436.
Putsep, K. et al., "Antibacterial Peptide from *H. pylori*," Nature, vol. 398, Apr. 22, 1999.
Charbit, A., et al., "Presentation of Two Epitopes of the preS2 Region of Hepatitis B Virus on Live Recombinant Bacteria," The Journal of Immunology, 1987, The American Association of Immunologists, vol. 139, 1658-1664, No. 5, Sep. 1, 1987.
Agterberg, M. et al., "Outer Membrane PhoE Protein of *Escherichia coli* as a Carrier for Foreign Antigenic Determinants: Immunogenicity of Epitopes of Foot-and-Mouth Disease Virus," Vaccine, vol. 8, Feb. 1990, Butterworth & Co. Ltd.
Felici, F. et al., "Section of Antibody Ligands from a Large Library of Oligopeptides Expressed on a Multivalent Exposition Vector," J.Mol. Biol. 1991, 222, 301-310.
Fuchs, P. et al., "Targeting Recombinant Antibodies to the Surface of *Escherichia coli*: Fusion to a Peptidoglycan Associated Lipoprotein," Bio/Technology, vol. 9, Dec. 1991.
Francisco, J.A.., et al., "Transport and Anchoring of β-lactamase to the External Surface of *Escherichia coli*." Proc. Natl. Acad. Sci. USA, vol. 89, pp. 2713-2717, Apr. 1992.
Hedegaard, L. et al., "Type 1 Fimbriae of *Escherichia coli* as Carriers of Heterologous Antigenic Sequences," Gene, 85, 1989, 115-124.
Jung, H.C., et al., "Surface Display of *Zymomonas mobilis* Levansucrase by Using the Ice-nucleation Protein of *Pseudomonas Syringae*," Nature Biotechnology, vol. 16, Jun. 1998.
Jung, H.C., et al., "Expression of Carboxymethylcellulase on the Surface of *Escherichia coli* Using *Pseudomonas* Syringae Ice Nucleation Protein," Enzyme and Microbial Technology 22:348-354, 1998, New York, USA.
Lee, J.S., et al., "Surface-displayed Viral Antigens on *Salmonella* Carrier Vaccine," Nature Biotechnology, vol. 10, Jun. 2000.

(Continued)

*Primary Examiner*—Nancy Vogel
(74) *Attorney, Agent, or Firm*—LaRiviere, Grubman & Payne, LLP

(57) ABSTRACT

The present invention relates to a method for expressing each of peptide antibiotics P5 3 and Ana13 35 having amphiphilicity and showing antibacterial, antifungal and anticancer activities 61, 63, 65, 67, 69, 71, on the microbial surface, using a vector containing outer membrane protein genes (pgsBCA) that are derived from *Bacillus* sp. strains and involved in the synthesis of poly-gamma-glutamate. Moreover, the present invention relates to lactic acid-forming bacteria having each of the peptide antibiotics P5 15 and Ana13 43 expressed on their surface, and the use thereof.

According to the present invention, the peptide antibiotics can be expressed on the surface of various microorganisms transformed with the surface expression vectors. The inventive method for the surface expression of the peptide antibiotics allows the peptide antibiotics to be mass-produced without a purification process. Thus, the inventive method has very high industrial applicability. Further, the present invention can be applied to other peptide antibiotics besides P5 3 and Ana13 35.

9 Claims, 15 Drawing Sheets

OTHER PUBLICATIONS

Kornacker, M.G. and Pugsley, A.P., "The normally periplasmic enzyme β-lactamase is Specifically and Efficiently Translocated through the *Escherichia coli* Outer Membrane when it is Fused to the Cell-surface Enzyme Pullulanase," Molecular Microbiology, 1990, 4(7), 1101-1109.

Klauser, T., et al., "Extracellular Transport of Cholera Toxin B Subunit Using Neisseria IgA Protease β-domain: Conformation-dependent Outer Membrane Translocation," The EMBO Journal, vol. 9, No. 6, pp. 1991-1999, 1990.

* cited by examiner

FIGURES

SEQUENCE LISTING

```
<160> NUMBER OF SEQ ID NOS: 9

<210> SEQ ID NO 1
<211> LENGTH: 1182
<212> TYPE: DNA
<213> ORGANISM: Bacillus subtilis

<400> SEQUENCE: 1
atgggctggt tactcattat agcctgtgct gtcatactgg tcatcggaat attagaaaaa      60
cgacgacatc agaaaaacat tgatgccctc cctgttcggg tgaatattaa cggcatccgc     120
ggaaaatcga ctgtgacaag gctgacaacc ggaatattaa tagaagccgg ttacaagact     180
gttggaaaaa caacaggaac agatgcaaga atgatttact gggacacacc ggaggaaaag     240
ccgattaaac ggaaacctca ggggccgaat atcggagagc aaaaagaagt catgagagaa     300
acagtagaaa gaggggctaa cgcgattgtc agtgaatgca tggctgttaa cccagattat     360
caaatcatct ttcaggaaga acttctgcag gccaatatcg gcgtcattgt gaatgtttta     420
gaagaccata tggatgtcat ggggccgacg cttgatgaaa ttgcagaagc gtttaccgct     480
acaattcctt ataatggcca tcttgtcatt acagatagtg aatataccga gttctttaaa     540
caaaaagcaa aagaacgaaa cacaaaagtc atcattgctg ataactcaaa aattacagat     600
gagtatttac gtaattttga atacatggta ttccctgata acgcttctct ggcgctgggt     660
gtggctcaag cactcggcat tgacgaagaa acagcattta agggaatgct gaatgcgccg     720
```

-continued

```
ccagatccgg gagcaatgag aattcttccg ctgatcagtc cgagcgagcc tgggcacttt      780
gttaatgggt ttgccgcaaa cgacgcttct tctactttga atatatggaa acgtgtaaaa      840
gaaatcggtt acccgaccga tgatccgatc atcatcatga actgccgcgc agaccgtgtc      900
gatcggacac agcaattcgc aaatgacgta ttgccttata ttgaagcaag tgaactgatc      960
ttaatcggtg aaacaacaga accgatcgta aaagcctatg aagaaggcaa aattcctgca     1020
gacaaactgc atgacctaga gtataagtca acagatgaaa ttatggaatt gttaaagaaa     1080
agaatgcaca accgtgtcat atatggcgtc ggcaatattc atggtgccgc agagccttta     1140
attgaaaaaa tccacgaata caaggtaaag cagctcgtaa gc                        1182
```

<210> SEQ ID NO 2
<211> LENGTH: 447
<212> TYPE: DNA
<213> ORGANISM: Bacillus subtilis

<400> SEQUENCE: 2

```
atgttcggat cagatttata catcgcacta attttaggtg tactactcag tttaatttt       60 gcggaaaaaa cagggatcgt gccggcagga cttgttgtac cgggatattt aggacttgtg      120
tttaatcagc cggtctttat tttacttgtt ttgctagtga gcttgctcac ttatgttatc      180
gtgaaatacg gtttatccaa atttatgatt ttgtacggac gcagaaaatt cgctgccatg      240
ctgataacag ggatcgtcct aaaaatcgcg tttgattttc tatacccgat tgtaccattt      300
gaaatcgcag aatttcgagg aatcggcatc atcgtgccag gtttaattgc caataccatt      360
cagaaacaag gtttaaccat tacgttcgga agcacgctgc tattgagcgg agcgaccttt      420
gctatcatgt ttgtttacta cttaatt                                          447
```

<210> SEQ ID NO 3
<211> LENGTH: 1140
<212> TYPE: DNA
<213> ORGANISM: Bacillus subtilis

<400> SEQUENCE: 3

```
atgaaaaaag aactgagctt tcatgaaaag ctgctaaagc tgacaaaaca gcaaaaaaag       60 aaaccaata agcacgtatt tattgccatt ccgatcgttt ttgtccttat gttcgctttc      120
atgtgggcgg aaaagcgga acgccgaag gtcaaaacgt attctgacga cgtactctca      180
gcctcatttg taggcgatat tatgatggga cgctatgttg aaaaagtaac ggagcaaaaa      240
ggggcagaca gtattttttca atatgttgaa ccgatcttta gagcctcgga ttatgtagca      300
ggaaactttg aaacccggt aacctatcaa agaattata acaagcaga taagagagatt      360 catctgcaga cgaataagga atcagtgaaa gtcttgaagg atatgaattt cacggttctc      420
aacagcgcca acaaccacgc aatggattac ggcgttcagg gcatgaaaga tacgcttgga      480
gaatttgcga agcaaaacct tgatatcgtt ggagcgggat acagcttaag tgatgcgaaa      540
aagaaaattt cgtaccagaa agtcaacggg gtaacgattg caacgcttgg ctttaccgat      600
gtgtccggga aggtttcgc ggctaaaaag aatacgccgg gcgtgctgcc cgcagatcct      660
gaaatcttca tccctatgat ttcagaagcg aaaaaacatg ctgacattgt tgttgtgcag      720
tcacactggg gccaagagta tgacaatgat ccaaacgacc gccagcgcca gcttgcaaga      780
gccatgtctg atgcgggagc tgacatcatc gtcggccatc atccgcacgt cttagaaccg      840
attgaagtat ataacggaac cgtcattttc tacagcctcg gcaactttgt ctttgaccaa      900
```

```
ggctggacga gaacaagaga cagtgcactg gttcagtatc acctgaagaa aaatggaaca      960
ggccgctttg aagtgacacc gatcgatatc catgaagcga cacctgcacc tgtgaaaaaa     1020
gacagcctta aacagaaaac cattattcgc gaactgacga aagactctaa tttcgcttgg     1080
aaagtagaag acgaaaaact gacgtttgat attgatcata gtgacaaact aaaatctaaa     1140
```

<210> SEQ ID NO 4
<211> LENGTH: 61
<212> TYPE: DNA
<213> ORGANISM: Artificial Sequence
<220> FEATURE:
<223> OTHER INFORMATION: primer

<400> SEQUENCE: 4

```
gatccaagtg aagaaactg ctcaagaaac cgctgctcaa gaagctgctc aagaaactgt        60
a                                                                       61
```

<210> SEQ ID NO 5
<211> LENGTH: 62
<212> TYPE: DNA
<213> ORGANISM: Artificial Sequence
<220> FEATURE:
<223> OTHER INFORMATION: primer

<400> SEQUENCE: 5

```
aagctacagt tcttgagca gcttcttgag cagccggttt cttgagcagt tcttccact         60 tg                                                                       62
```

<210> SEQ ID NO 6
<211> LENGTH: 64
<212> TYPE: DNA
<213> ORGANISM: Artificial Sequence
<220> FEATURE:
<223> OTHER INFORMATION: primer

<400> SEQUENCE: 6

```
gatccgcgaa gaaggtgttc aaacgcctgg agaagctgtt tagcaaaatc tggaactgga      60
agta                                                                    64
```

<210> SEQ ID NO 7
<211> LENGTH: 64
<212> TYPE: DNA
<213> ORGANISM: Artificial Sequence
<220> FEATURE:
<223> OTHER INFORMATION: primer

<400> SEQUENCE: 7

```
aagctacttc cagttccaga ttttgctaaa cagcttctcc aggcgtttga acaccttctt      60
cgcg                                                                    64
```

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8

```
ctgggatccc aaggtatgtt gcccgtttg                                         29
```

<210> SEQ ID NO 9
<211> LENGTH: 30

```
<212> TYPE: DNA
<213> ORGANISM: Artificial Sequence
<220> FEATURE:
<223> OTHER INFORMATION: primer

<400> SEQUENCE: 9
tgaagcttat taggacgatg ggatgggaat                                            30
```

SURFACE EXPRESSION METHOD OF PEPTIDES P5 AND ANAL3 USING THE GENE ENCODING POLY-GAMMA-GLUTAMATE SYNTHETASE

TECHNICAL FIELD

The present invention relates to a method for expressing each of peptide antibiotics P5 and Anal3 on the surface of microorganisms, lactic acid-forming bacteria having each of the peptide antibiotics P5 and Anal3 expressed on their surface, and the use thereof, using outer membrane protein genes (pgsBCA) that are derived from *Bacillus* sp. strains and involved in the synthesis of poly-gamma-glutamate.

BACKGROUND ART

Recently, the antibiotic resistance of bacteria caused by the inappropriate use of antibiotics becomes a severe problem. In fact, the rate at which bacteria exhibit resistance to new antibiotics is faster than the rate at which the analogues of the new antibiotics are developed. The condition preceding the antibiotic resistance of bacteria is that bacteria have tolerance to antibiotics. The bacteria showing tolerance to antibiotics stop their growth in the presence of a general concentration of antibiotics, but do not ultimately die.

Tolerance occurs since the activity of bacterial autolytic enzymes, such as autolysin, does not occur when antibiotics inhibit cell wall synthetase. As a result of the above fact, penicillin activates endogenous hydrolytic enzymes to kill bacteria, but the bacteria inhibit the activity of the enzymes such that they survive even in antibiotics treatment. Actually, since all bacteria showing antibiotic resistance are known as having tolerance as well, there is a need for the development of new antibiotics capable of killing bacteria with antibiotic resistance.

Thus, many studies to develop new antibiotics against bacteria are being conducted, and among them, the development of peptides showing antibacterial activity is predominant. In the natural system, bacteria synthesize peptides or small organic molecules to be able to kill adjacent bacteria, and such bacteriocins are structurally classified into the following three categories: (1) lantibiotics, (2) non-lantibiotics, and (3) antibiotics secreted by a signal peptide.

Animals, including insects, also produce naturally occurring peptides. Such peptide antibiotics are structurally classified into the following three categories: (1) cysteine-rich sheet peptides, (2) cysteine-rich helical amphiphilic molecules, (3) proline-rich peptides. These antibacterial peptides are known to play an important role in a host defense and a native immune system.

Such antibacterial peptides have various structures depending on their amino acid sequence, and among such structures, the one that is most frequently present is an amphiphilic alpha-helical structure with no cysteine residues, such as cecropin that is an antibacterial peptide found in insects. Many studies on the antibacterial activity of amphiphilic peptides were conducted, and the amphiphilic peptides reported till now include magainin 2 (MA), cecropin A (CA), melittin (ME) and the like.

DISCLOSURE OF INVENTION

While it was known that some sequences of such peptides could be recombined to produce conjugated peptides, thereby producing new synthetic peptides having excellent antibacterial, antifungal and anticancer activities, the present inventors synthesized new peptide antibiotics P5, using a peptide (CA-MA) template comprising a conjugate of cecropin A (CA) and magainin 2 (MA) each having amphiphilicity, and confirmed that the peptide antibiotics P5 had antibacterial, antifungal and anticancer activities.

Among amphiphilic peptides, a RPL1 protein derived from *Helicobacter pylori*, a gram-negative anaerobic bacterium, has a perfect amphiphilic helical structure at the amino terminal. It is known that such an amphiphilic peptide has a structure similar to a cell membrane lipid component, and thus, has the mechanism of binding to the cell membrane lipid of a microorganism to either break the microbial cell membrane or influence the potential of the cell membrane to break the microorganism. By the present inventors, some of certain sequences of the RPL1 protein derived from *Helicobacter pylori* with amphiphilicity were substituted with other amino acids to design peptide derivatives with increased hydrophobic sites so as to have an amphiphilic structure, thereby producing synthetic peptide Anal3, and also the present inventors found that the peptide Anal3 had antibacterial, antifungal and anticancer activities.

Such a new antibiotics has an advantage in that it has a low possibility of causing tolerance since it exhibits antibacterial activity by an activity mechanism different from the prior antibiotics. Thus, the peptide antibiotics have a very high industrial applicability in the pharmaceutical and food field, etc. However, the greatest hindrance in industrially applying the above peptide antibiotics is that it cannot be provided at low prices and large amounts. For example, the production of the peptide antibiotics by chemical synthesis has the problem of low economic efficiency, and there is an attempt to produce the peptide antibiotics by a genetic engineering technique using microorganisms, but it has problems in that the peptide antibiotics is very difficult to purify due to its low expression level, and a host for expressing the peptide is killed by the peptide being expressed. As a solution to such problems, there is an attempt to express, purify and produce peptides using a gene of neutralizing the host toxicity of the peptides, but it also has problems in terms of purification and economic efficiency. Thus, there is an urgent need for a method that can mass-produce peptide substances in a simpler and easier manner, and makes purification simple or unnecessary, to allow the peptide substances to be industrially applied.

A technology of anchoring and expressing the desired protein on the surface of microorganisms is called the "cell surface display technology". This cell surface display technology, which expresses a foreign protein on the microbial surface, using microbial surface proteins (e.g., bacteria or yeasts) as a surface anchoring motif, can be used a wide range of applications, including the production of live recombinant vaccines, the construction and screening of peptide/antibody libraries, whole cell absorbents, and whole cell bioconversion catalysts. Namely, the application range of this technology is determined depending on what protein is expressed on the cell surface, and thus, the industrial applicability of this cell surface display technology can seem to be significant.

For successful cell surface expression, a surface-anchoring motif is most important. The selection and development of a surface-anchoring motif capable of effectively expressing a foreign protein on the cell surface becomes the core of this technology. For this reason, a surface-anchoring motif having the following properties should be selected: (1) it should have a secretion signal that helps a foreign protein passing through the cell inner membrane to the cell surface; (2) it should have a target signal that helps the foreign protein to be stably attached to the surface of the cell outer membrane; (3) it should be expressed on the cell surface at large amounts but have little or no effect on the growth of cells; and (4) it should have no connection with the size of proteins and be stably expressed without changing the three-dimensional structure of the foreign protein. However, surface-anchoring motifs satisfying all such conditions are not yet developed, and the motifs developed till now remain at a level at which the above-mentioned problems are mitigated.

The surface-anchoring motifs known and used till now are broadly classified into the following proteins: outer membrane proteins, lipoproteins, secretory proteins, and surface proteins, such as flagellum protein. In the case of gram-negative bacteria, proteins present in the cell outer membrane, such as LamB, PhoE, and OmpA, were mainly used. Also, the expression of a foreign protein was attempted using lipoprotein TraT, peptidoglycan-associated lipoprotein (PAL), Lpp, FimA, fimbriae protein, such as the FimH adhesion protein of type 1 fimbriae, or pili protein, such as a PapA pilu subunit, as a surface-anchoring motif. In addition, there is a report that ice nucleation protein), *Klebsiela oxytoca* pullulanase, the IgA protease of *Neiseria;* and the like, are used as the surface-anchoring motif. In the case of gram-positive bacteria, there is a report that a malaria antigen was effectively expressed using *Staphylococcus aureus*-derived protein A as the surface-anchoring motif, and also a report that the surface coat protein of lactic acid-forming bacteria was used in surface expression.

The present inventors conducted intensive studies on the use of *Bacillus* sp.-derived poly-gamma-glutamate synthetase genes (pgsBCA) as a new surface anchoring motif, and as a result, using the pgsBCA proteins, the present inventors developed a new vector of effectively expressing a foreign protein on the microbial surface, and also a method of expressing the foreign protein on the microbial surface at large amounts. In the above mentioned patent application, the present inventors stated that outer membrane proteins, which are involved in the synthesis of poly-gamma-glutamate, had the following many advantages as a surface-anchoring motif of expressing a foreign protein on the cell surface, because of the structure and characteristic of their amino acid primary sequence: (1) the outer membrane proteins, which are involved in the synthesis of poly-gamma-glutamate, can be expressed on the cell surface at large amounts for the synthesis and extracellular secretion of poly-gamma-glutamate, (2) the outer membrane proteins, which are involved in the expressed poly-gamma-glutamate, are stably maintained even at the resting stage of the cell cycle; (3) particularly the pgsA gene is protruded from the cell surface; (4) the outer membrane proteins (pgsBCA), which are involved in the synthesis of poly-gamma-glutamate, are derived from gram-positive bacteria and can be expressed in various gram-positive bacteria and also stably expressed on the surface of gram-negative bacteria; and (5) even if only one or two or more of the genes pgsB, pgsC and pgsA, which encode a poly-gamma-glutamate synthetase complex, is contained in a microbial surface expression vector, the surface expression of a peptide antibiotics will be possible.

A main object of the present invention is to provide a means capable of mass-producing peptide antibiotics in a simple, easy and safe manner. Concretely, an object of the present invention is to provide a surface expression vector by which amphiphilic peptide antibiotics P5 and Anal3 showing antibacterial, antifungal and anticancer activities can be expressed on the cell surface, using as a surface-anchoring motif, an outer membrane protein gene(pgsBCA) involved in the synthesis of derived from *Bacillus* sp. such that a foreign protein can be effectively expressed on the microbial surface.

Another object of the present invention is to provide a method for the surface expression of peptides, which allows the peptide antibiotics to be mass-produced from non-toxic microorganisms transformed with the above surface expression vector, in a simple, easy and simple manner.

Still another object of the present invention is to provide a use as antibacterial or antifungal substances of either the live microorganisms having the above peptide antibiotics expressed on their surface, or a suspension obtained by inactivating the microorganisms.

To achieve the above objects, the present invention provides a vector for the surface expression of antibiotics, which comprises: one or more than two genes of pgsB, pgsC and pgsA encoding a poly-gamma-glutamate synthetase complex; and a gene encoding an amphiphilic peptide antibiotics with antibacterial, antifungal and anticancer activities.

In the present invention, the pgsB, pgsC and pgsA genes preferably have the base sequences shown in SEQ ID NO: 1, SEQ ID NO: 2 and SEQ ID NO: 3, respectively. Also, the inventive vector preferably contains the pgsA gene among the genes encoding the poly-gamma-glutamate synthetase complex. The amphiphilic peptide antibiotics with antibacterial, antifungal and anticancer activities preferably has an identity with either peptide P5 that is encoded by the base sequence of SEQ ID NO: 4, or peptide Anal3 that is encoded by the base sequence of SEQ ID NO: 6.

Also, the present invention provides vectors pHCE1LB: pgsA-P5 and pHCE1LB:pgsA-Anal3 for the surface expression of antibiotics, which can express the antibiotics on the surface of gram-negative and gram-positive bacteria.

Moreover, the present invention provides microorganisms transformed with the above vectors for the surface expression of antibiotics. Particularly, the present invention provides *E. coli* (KCTC 10350BP) transformed with the vector pHCE1LB:pgsA-P5, and *E. coli* (KCTC 10348BP) transformed with the vector pHCE1LB:pgsA-Anal3.

Furthermore, the present invention provides lactic acid-forming bacteria transformed with the vectors for the surface expression of antibiotics. Particularly, the present invention provides lactic acid-forming bacteria transformed with the pHCE1LB:pgsA-P5 or pHCE1LB:pgsA-Anal3 vector.

Also, the present invention provides a method for producing lactic acid-forming bacteria having peptide antibiotics P5 or Anal3 expressed on their surface, which comprises the step of culturing the transformed lactic acid-forming bacteria.

In addition, the present invention provides a pharmaceutical composition for antibacterial, antifungal and anticancer applications, which comprises, as an active ingredient, either the lactic acid-forming bacteria produced by the above method and having the peptide antibiotics P5 or Anal3 expressed on their surface, or a suspension of the lactic acid-forming bacteria containing the peptide antibiotics P5.

The active ingredient of the pharmaceutical composition according to the present invention is preferably heat-treated.

BRIEF DESCRIPTION OF THE DRAWINGS

The above and other objects, features and advantages of the present invention will be apparent from the following detailed description of the preferred embodiments of the invention in conjunction with the accompanying drawings.

MODES FOR CARRYING OUT THE INVENTION

Figure 1:
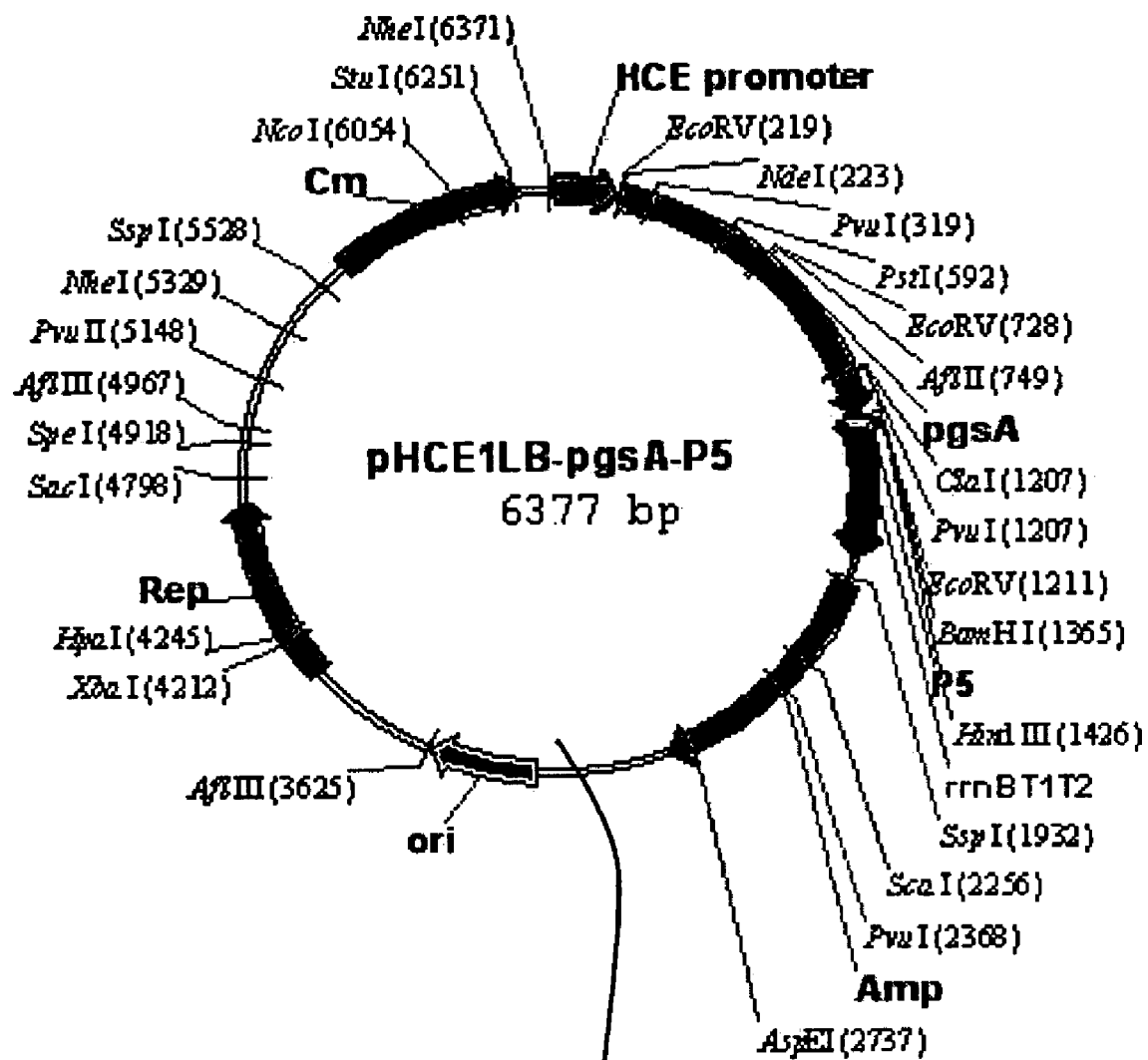
FIG. 1 is a genetic map of the transformation vector pHCE1LB:pgsA-P5 for surface expression, which uses gram-negative and gram-positive microorganisms as hosts.

Reference will now be made in detail to the preferred embodiment of the present invention, an example of which is illustrated in the accompanying drawings.

In the present invention, a pHCE1LB plasmid was used as a basic vector such that it could be replicated and screened in both gram-negative bacteria and gram-positive bacteria. The vector pHCE1LB comprises a HCE promoter for high-level constitutive expression, a cloning site having various restriction enzyme sites, at the back of the promoter, an origin allowing replication in gram-negative bacteria, and an ampicillin antibiotics marker. In addition, the pHCE1LB vector has a *Lactobacillus*-derived origin allowing replication in gram-positive bacteria, and a chloramphenicol antibiotics marker. The utilization of this vector is described in detail in WO 03/14360 that was filed earlier by the present inventors.

The lactic acid-forming bacteria expressing peptide antibiotics on their surface according to the present invention exhibit significantly strong antifungal activity against pathogenic fungi, such as *Candida albicans* 51, *Trichosporon beigelii*, *Saccharomyces cerevisiae* and *Trichophyton rubrum* 57. In addition, the inventive lactic acid-forming bacteria expressing the peptide antibiotics on their surface do not show antibacterial action against other lactic acid-forming bacteria. Accordingly, the inventive microorganisms (e.g., lactic acid-forming bacteria) expressing the peptide antibiotics on their surface, or peptide antibiotics purified from the microorganisms, show excellent antibacterial, antifungal and anticancer activities while having no cytotoxicity, and thus, can be advantageously used as antibacterial, antifungal and anticancer substances harmless to the human body.

The present invention will hereinafter be described in further detail by examples. It will however be obvious to a person skilled in the art that these examples are given for illustrative purpose only, and the scope of the present invention is not limited to or by these examples.

In the following examples, although the peptide antibiotics P5 and Anal3 were particularly used as foreign peptides, other peptides showing specific activities (e.g., antibacterial, antivirus, antifungal, anti-inflammatory and anti-allergic activities) will also be used.

Also, although gram-positive bacteria *Lactobacillus* were used in the following examples, it will be obvious to a person skilled in the art that gram-positive or gram-negative bacteria other than such bacteria will be transformed by the inventive method to give the same results.

In addition, although the outer membrane protein genes pgsBCA, which is derived from *Bacillus subtilis* var. *chungkookjang* (KCTC 0697BP) and involved in the synthesis of poly-gamma-glutamate, was used in the following examples, it will also be within the scope of the present invention to use pgsBCA genes derived from other *Bacillus* sp. strains producing poly-gamma-glutamate. For example, it will also be within the scope of the present invention to either produce a surface expression vector or surface-express a peptide antibiotics using pgsBCA genes derived from other strains, which has more than 80% homology with the base sequence of pgsBCA genes present in *Bacillus subtilis* var. *chungkookjang*.

Moreover, in the following examples, although the surface expression vector was produced using only the pgsA gene among the pgsBCA genes, it will be understood that the construction of the surface expression vector using all or parts of the pgsBCA genes will also be within the scope of the present invention.

EXAMPLE 1

Production of Transformation Vector pHCE1LB:A-P5 For Surface Expression, and Surface Expression of Peptide P5 Fused with pgsA (1) Production of Transformation Vector pHCE1LB:pgsA-P5 1 for Surface Expression Against Peptide Antibiotics P5

FIG. 1 is a genetic map of the transformation vector pHCE1LB:pgsA-P5 1 for surface expression, which uses gram-negative and gram-positive microorganisms as hosts. The pgsA gene among the genes pgsBCA, which are derived from *Bacillus subtilis* var. *chungkookjang* (KCTC 0697BP) and involved in the synthesis of poly-gamma-glutamate, was inserted into the basic vector pHCE1LB using gram-negative and gram-positive microorganisms as hosts, thereby constructing intermediate vector pHCE1LB. In order to introduce peptide antibiotics P5-encoding gene into the intermediate vector, the intermediate vector was added with an oligonucleotide having the base sequences of SEQ ID NO: 4 and SEQ ID NO: 5, and denatured for 5 minutes at 95° C., followed by annealing at 37° C. for 1 hour, thereby giving a double helical base with a 65-bp size.

SEQ ID NO: 4
5'-ga tcc aag tgg aag aaa ctg ctc aag aaa ccg ctg ctc aag aag ctg ctc aag aaa ctg ta-3':

SEQ ID NO: 5
5'-aag cta cag ttt ctt gag cag ctt ctt gag cag ccgg ttt ctt gag cag ttt ctt cca ctt g-3'

Both ends of the annealed double helical base having SEQ ID NO:4 and SEQ ID NO:5 were so constructed that they have recognition sites for restriction enzymes BamH I and Hind III present in surface expression vector pHCE1LB:pgsA. The annealed P5 gene was linked with the surface expression vector pHCE1LB:pgsA treated with restriction enzymes BamH I and Hind III such that the translation codon of the P5 gene was fitted with the C-terminal of the outer membrane gene pgsA (i.e., ORF is formed). The transformation vector pHCE1LB:pgsA-P5 thus produced is shown in FIG. 1.

*E. Coli* was transformed with the surface expression vector pHCE1LB:pgsA-P5 1 constructed as described above and the transformed *E. coli* was deposited under the accession number KCTC 10350BP with the Korean Collection for Type Cultures (KCTC), Korean Research Institute of Bioscience and Biotechnology located at 52 Oun-dong, Yusong-ku, Taejon 305-333, Republic of Korea. BIOLOGICAL DEPOSIT: A copy of the original deposit receipt for *Escherichia coli* JM1O9/pHCE1LB:pgsA-P5 with accession number KCTC 10350BP, received Oct. 04, 2002 at the Korea Research Institute of Bioscience and Biotechnology (KRIBB) has been provided. All restrictions on the availability to the public of the material so deposited will be irrevocably removed upon the granting of a patent.

(2) Surface Expression of pgsA-fused Peptide P5 Using *Lactobacillus casei* Transformed With Surface Expression Vector pHCE1LB:pgsA-P5

Figure 2:
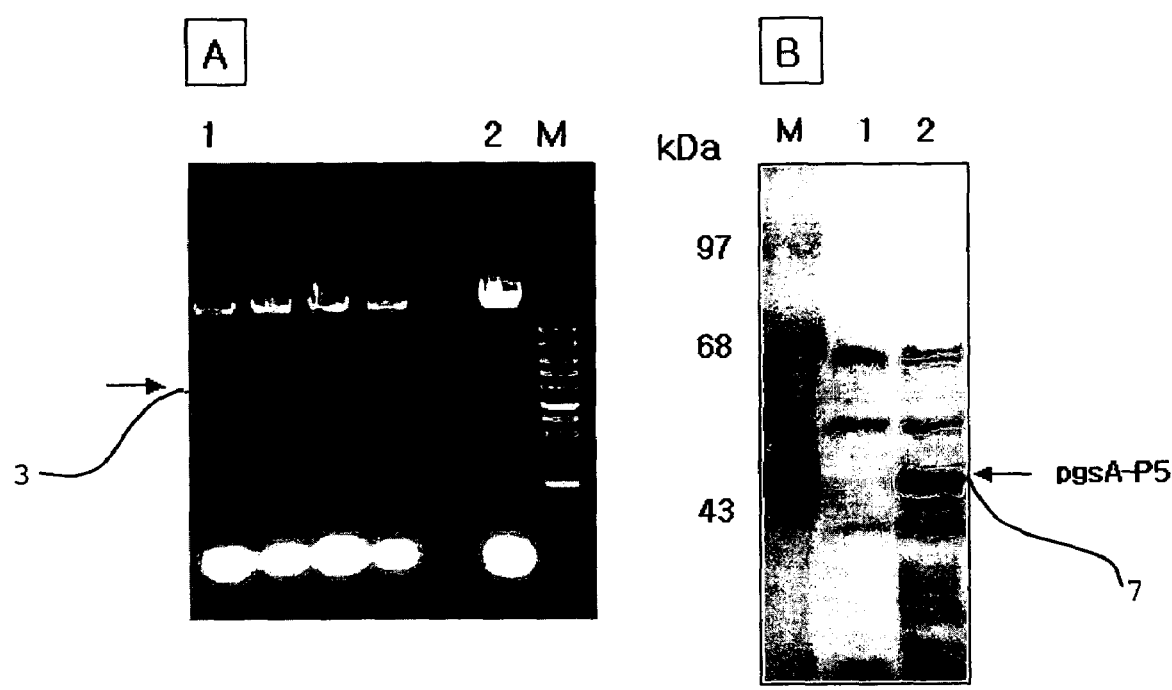
FIG. 2A is a photograph showing a transformation vector plasmid for surface expression separated from the lactic acid-forming bacteria transformed with a transformation vector (pHCE1LB:pgsA-P5) for surface expression.
FIG. 2B is a photograph showing the protein expression pattern of peptide antibiotics P5 fused with a pgsA gene, in which the protein expression pattern was analyzed by Western immunoblotting with a specific antibody.

*Lactobacillus casei* transformed with the surface expression vector pHCE1LB:pgsA-P5 3 was cultured and grown in 200 ml MRS medium containing 50 mg/L chloramphenicol, and examined for the presence of a pHCE1LB:pgsA-P5 plasmid in *Lactobacillus* (FIG. 2A), and then examined for the expression of the peptide P5 fused with the pgsA gene 7 (FIG. 2B). The expression of the peptide antibiotics P5 fused with the C-terminal of the gene pgsA, which is involved in the synthesis of poly-gamma-glutamate, was analyzed by SDS-polyacrylamide gel electrophoresis and Western immunoblotting using a specific antibody to the pgsA gene. FIG. 2A is a photograph showing a transformation vector plasmid for surface expression 3 separated from the lactic acid-forming bacteria transformed with a transformation vector (pHCE1LB:pgsA-P5) for surface expression, and FIG. 2B is a photograph showing the protein expression pattern of peptide antibiotics P5 fused with a pgsA gene 7, in which the protein expression pattern was analyzed by Western immunoblotting with a specific antibody.

Concretely, *Lactobacillus casei* transformed with the pHCE1LB:pgsA-P5 plasmid was grown in MRS medium (*Lactobacillus* MRS, Becton Dickinson and Company Sparks, USA) at 37° C., to induce the surface expression of the peptide P5. The protein was collected from the above *Lactobacillus*, and denatured to prepare a sample. The sample was analyzed by SDS-polyacrylamide gel electrophoresis (FIG. 2A), and the protein fractions were transferred to a polyvinylidene-difluoride (PVDF) membrane (Bio-Rad). The PVDF membrane to which the protein fractions had been transferred was blocked by shaking in a blocking buffer solution (50 mM Tris HCl, 5% skim milk, pH 8.0) for one hour, and a rabbit polyclonal primary antibody to the pgsA gene was 1,000-fold diluted in the blocking buffer solution, and reacted with the protein for 12 hours. After the reaction, the membrane was washed with buffer solution, and a biotin-conjugated rabbit secondary antibody was 1,000-fold diluted in the blocking buffer solution and reacted with the protein for 4 hours. After the reaction, the membrane was washed with buffer solution, and reacted with an avidin-biotin reagent for 1 hour, followed by washing. The washed membrane was developed by the addition of $H_2O_2$ as a substrate and DAB solution as a color development reagent, and the specific binding between the specific antibody to the pgsA gene and the fusion protein was examined (FIG. 2B). In FIG. 2B, Lane 1 represents *Lactobacillus casei* that is a non-transformed host cell, and Lane 2 represents a transformed pHCE1LB:pgsA-P5/*Lactobacillus casei*. As shown in FIG. 2B, the fusion protein band of about 44 KDa caused by the pHCE1LB:pgsA-P5 plasmid was detected. Since the pgsA gene has about 41.8 KDa and the peptide P5 has about 2.2 KDa, it could be found that the 44-KDa band would be a fusion protein where the pgsA gene and the peptide P5 were fused to each other.

EXAMPLE 2

Measurement of Antifungal Activity of *Lactobacillus* Expressing Peptide Antibiotics P5 on Their Surface (1) In order to measure the antifungal activity of *Lactobacillus* which had been found in Example 1 to surface-express the peptide antibiotics P5, a visualization test of antifungal activity was conducted on pathogenic fungi *Candida albicans* (TIMM 1768) and *Trichosporon beigelii* (KCTC 7707).

Figure 3:
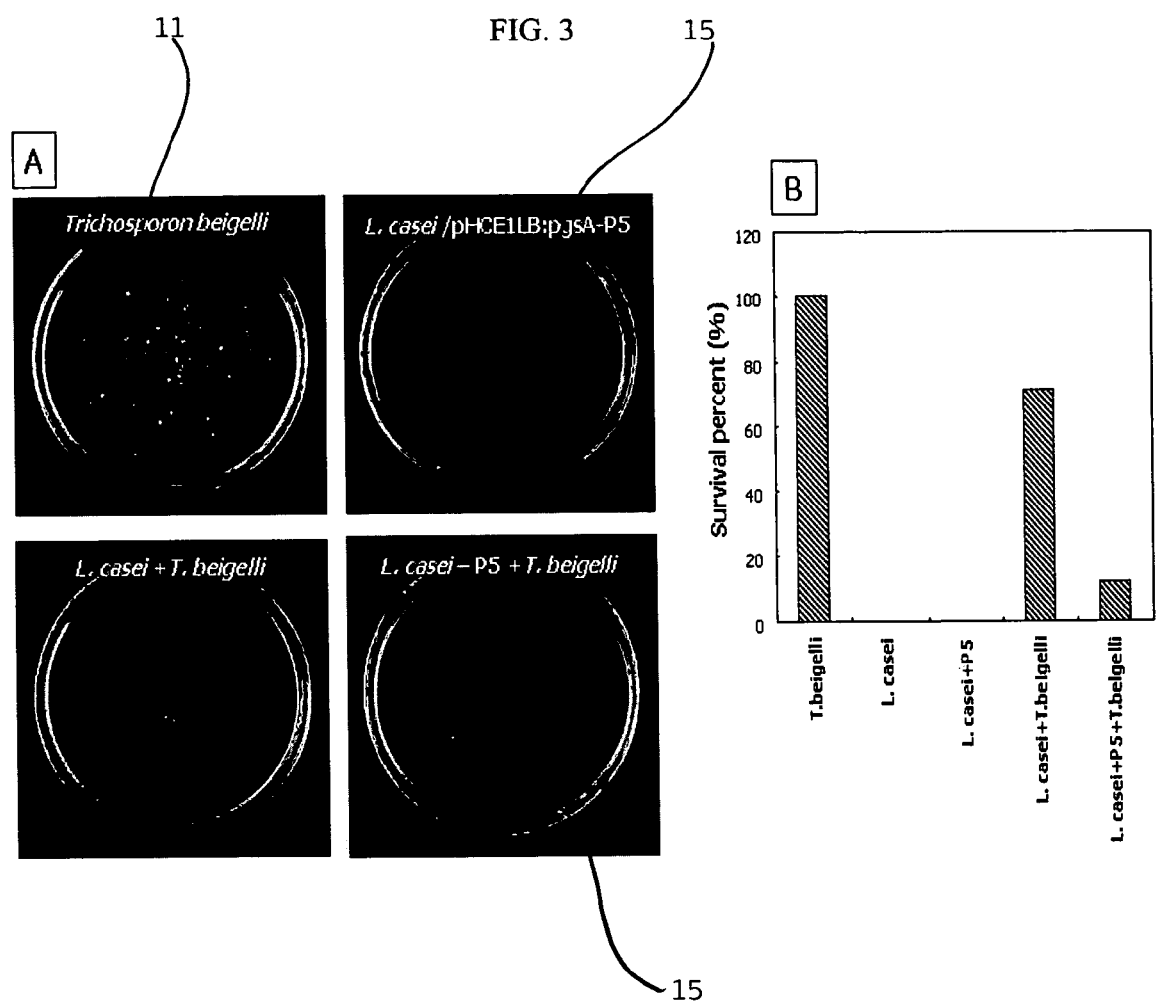
FIG. 3A is a plate photograph showing the antifungal activity against fungus *Trichosporon beigelli* of lactic acid-forming bacteria expressing peptide antibiotics P5 on their surface.
FIG. 3B is a graphic diagram showing the survival rate of *Trichosporon beigelli*.
Figure 4:
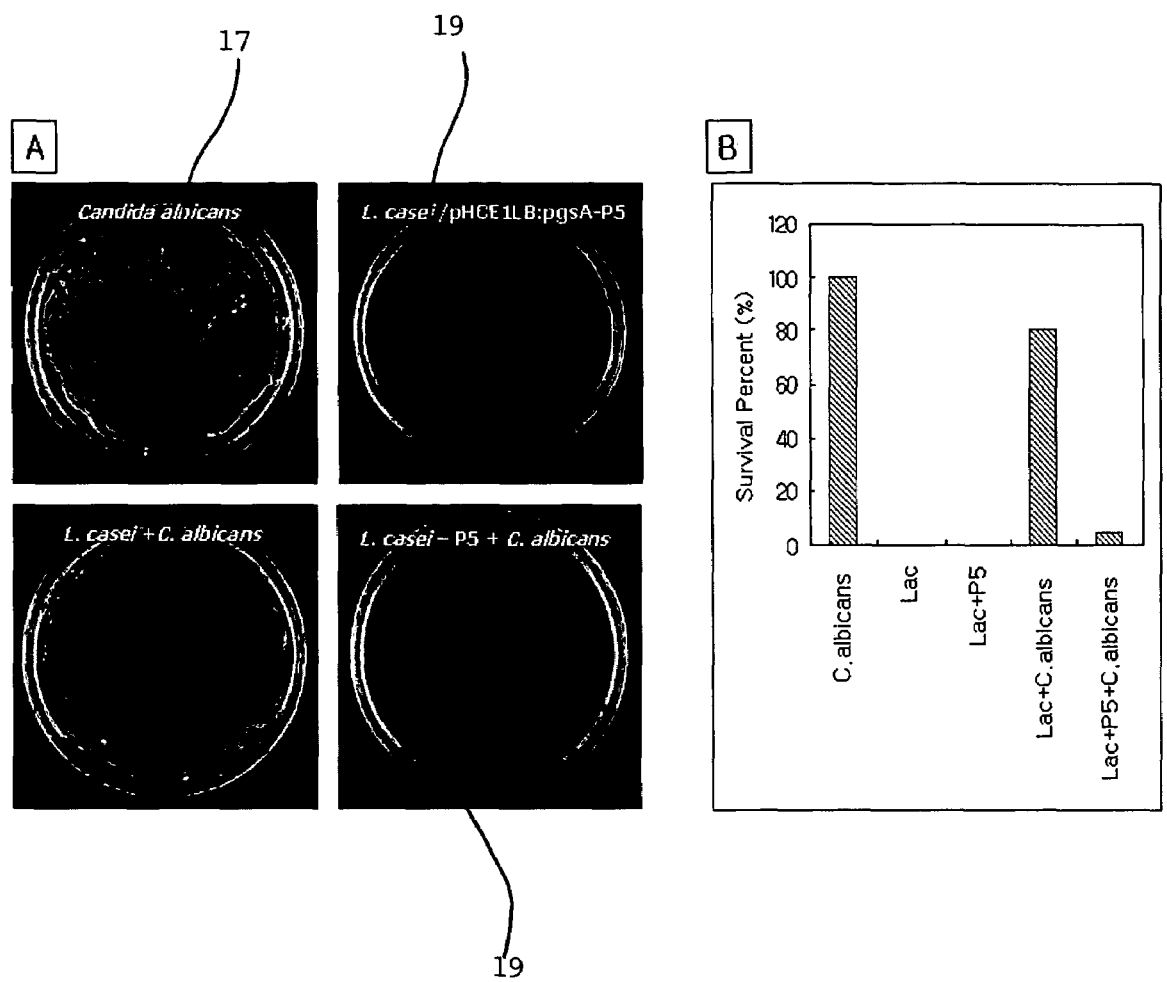
FIG. 4A is a plate photograph showing the antifungal activity against fungi *Candida albicans* of lactic acid-forming bacteria expressing peptide antibiotics P5 on their surface.
FIG. 4B is a graphic diagram showing the survival rate of *Candida albicans*.

Concretely, 50 μl of a PDB medium (20% potato infusion from, 2% Bacto-dextrose) containing $2 \times 10^3$ fungi was placed into each well of a 96-well plate, and 50 μl/well of MRS medium containing the *Lactobacillus* expressing the peptide P5 was successively diluted 1/2 times, and added to the fungi-containing well, followed by culturing at 37° C. for 16 hours. The cultured solution was plated on a PDB agar plate to visualize the strains. As a result, a large number of colonies could be found on the plates on which *Trichosporon beigelii* 11 and *Candida albicans* 21 themselves, and a mixture of such strains and wild-type *Lactobacillus*, had been plated. However, in the case where the *Lactobacillus* bacteria expressing the peptide antibiotics P5 on their surface had been added, it could be found that the growth of the fungi was completely inhibited so that colonies were not detected (FIGS. 3A and 4A). The survival rate of such fungi was graphically shown in FIGS. 3B and 4B. FIG. 3A is a plate photograph showing the antifungal activity against fungus *Trichosporon beigelli* 11 of lactic acid-forming bacteria expressing peptide antibiotics P5 on their surface 15, and FIG. 3B is a graphic diagram showing the survival rate of *Trichosporon beigelli*. Such results indicate that the *Lactobacillus* bacteria expressing the peptide antibiotics P5 on their surface exhibited excellent antifungal activity.

(2) Furthermore, the antifungal activity of inventive *Lactobacillus* bacteria expressing the peptide antibiotics P5 on their surface was examined by scanning electron microscopy (SEM) on *Candida albicans* (TIMM 1768) and *Trichosporon beigelii* (KCTC 7707). FIG. 4A is a plate photograph showing the antifungal activity against fungi *Candida albicans* 17 of lactic acid-forming bacteria expressing peptide antibiotics P5 19 on their surface, and FIG. 4B is a graphic diagram showing the survival rate of *Candida albicans*.

Concretely, by the method described in the part 1 of this Example, one of *Candida albicans* (TIMM 1768), *Trichosporon beigelii* (KCTC 7707) and *Saccharomyces cerevisiae* was cultured at 37° C. for 16 hours together with wild-type *Lactobacillus* or the *Lactobacillus* bacteria expressing the peptide P5 on their surface. Then, 0.2M phosphate buffer solution containing 5% glutaraldehyde was added to a given amount of the cultured solution at the same volume, and immobilized for 2 hours at 4° C. to prepare a sample. The sample was filtered through an Isopore filter (0.2 m pore size, Millipore, Bedford, Mass., USA), and washed with 0.1M Na-cacodylate buffer (pH 7.4). Next, the filter was treated with 1% osmium tetroxide, and washed with Na-cacodylate buffer containing 5% sucrose, and then dewatered stepwise with ethanol. The treated sample was freeze-dried, gold-coated and examined under a scanning electron microscope.

Figure 5:
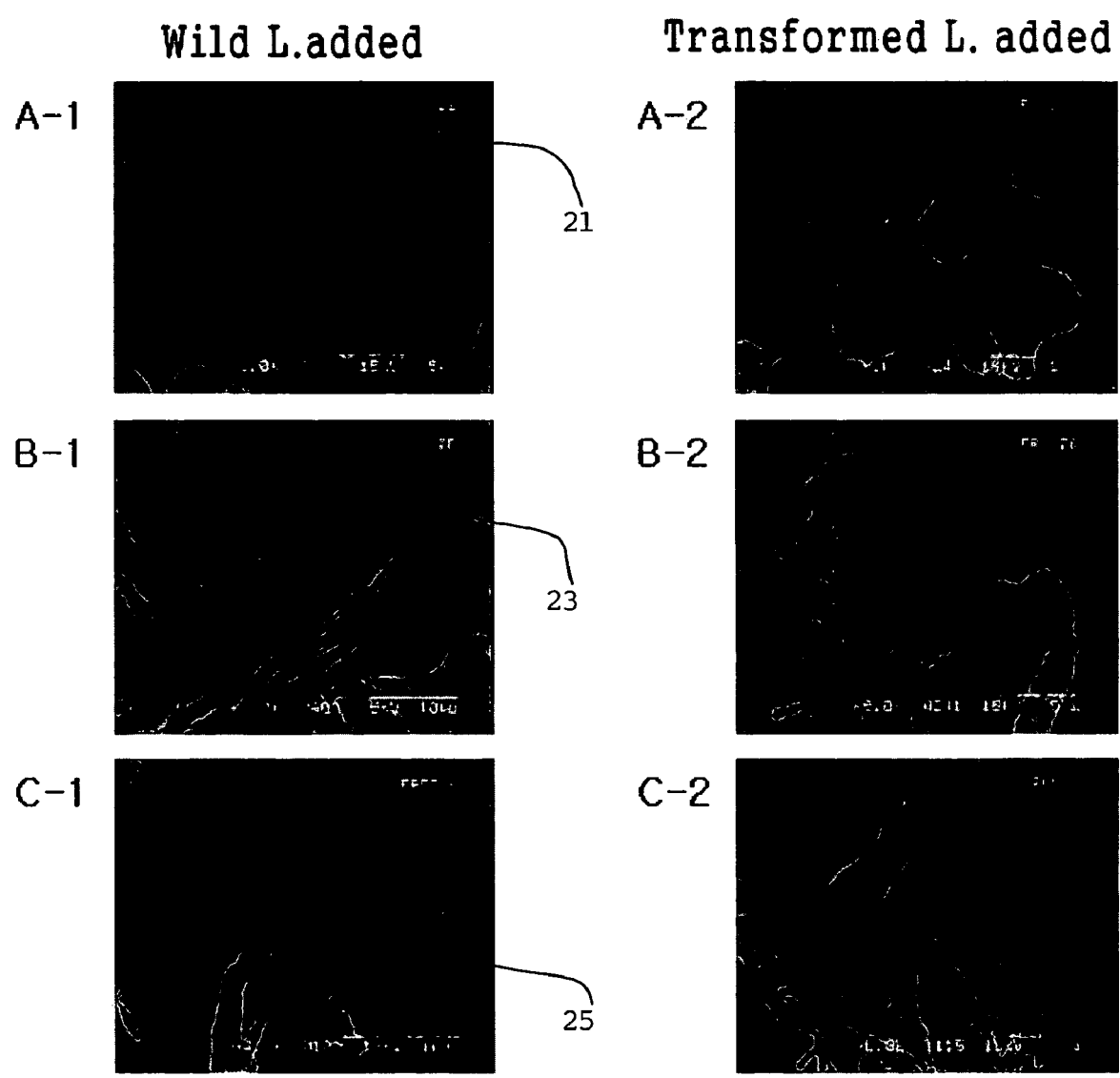
FIGS. 5A to 5C are scanning electron microphotographs showing the antifungal activity against fungi *Candida albicans* (5A), *Aspergillus flavus* (5B) and *Trichosporon beigelli* (5C) of lactic acid-forming bacteria expressing peptide antibiotics P5 on their surface.

As a result, in the cases where the *Lactobacillus* bacteria expressing the peptide antibiotics P5 on their surface had been added to *Candida albicans* 21 (FIG. 5A), *Trichosporon beigelii* 23 (FIG. 5B) and *Aspergillus flavus* 25 (FIG. 5C), it could be found that the cell breakdown of the fungi occurred at a larger amount than the case where the *Lactobacillus* bacteria expressing the peptide antibiotics P5 on their surface had not been added. FIGS. 5A to 5C are scanning electron microphotographs showing the antifungal activity against fungi *Candida albicans* 21(5A), *Aspergillus flavus* 23 (5B) and *Trichosporon beigelli* 25 (5C) of lactic acid-forming bacteria expressing peptide antibiotics P5 on their surface.

EXAMPLE 3

Production of Transformation Vector pHCE1LB:A-Anal3 for Surface Expression, and Surface Expression of Peptide Anal3 Fused with psA (1) Transformation vector pHCE1LB:A-Anal3 31, which can surface-express the peptide antibiotics Anal3, was produced in the same manner as in the part (1) of Example 1.

In order to introduce a peptide antibiotics Anal3-encoding gene into the intermediate vector pHCE1LB:pgsA, a genes having the base sequences of SEQ ID NO: 6 and SEQ ID NO: 7 and encoding the peptide Anal3 was annealed in the same manner as in Example 1, to give a 62-bp double helical sequence.

Figure 6:
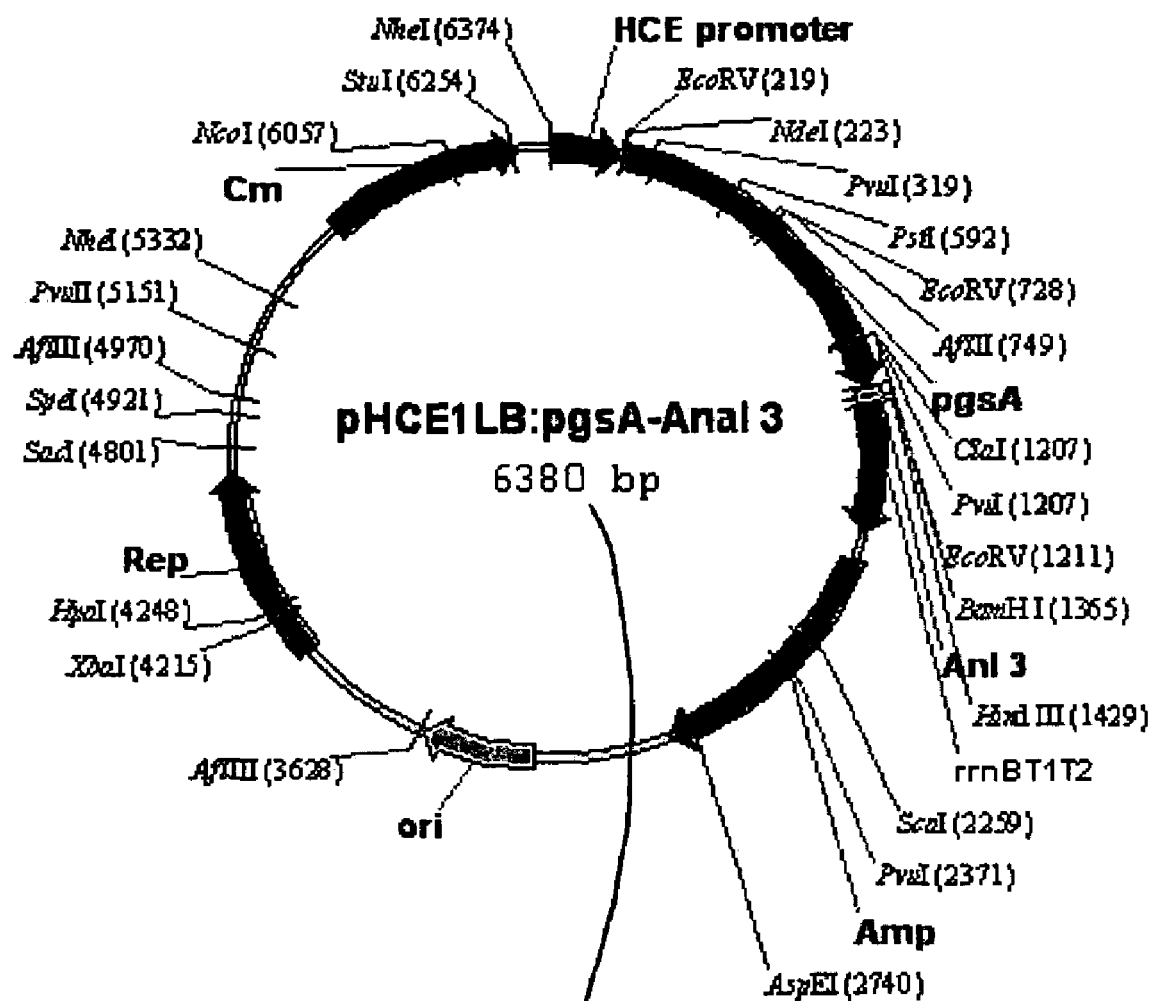
FIG. 6 is a genetic map of the transformation vector pHCE1LB:pgsA-Anal3 for surface expression, which uses gram-negative and gram-positive microorganisms as hosts.

SEQ ID NO 6
5'-ga tcc gcg aag aag gtg ttc aaa cgc ctg gag aag ctg ttt agc aaa atc tgg aac tgg aag ta-3':

SEQ ID NO: 7
5'-aag cta ctt cca gtt cca gat ttt gct aaa cag ctt ctc cag gcg ttt gaa cac ctt ctt cgc g-3':

Both ends of the double helical sequence formed by the base sequences of SEQ ID NO: 6 and SEQ ID NO: 7 were so constructed that they have recognition sites for restriction enzymes BamH I and Hind III, which are present in the surface expression vector pHCE1LB:pgsA. The annealed Anal3 gene was linked with the C-terminal of the outer membrane gene pgsA of the surface expression vector pHCE1LB:pgsA treated with BamH I and Hind III, such that its translation codon was fitted with the C-terminal. The transformation vector pHCE1LB:pgsA-Anal3 31 so produced is shown in FIG. 6. FIG. 6 is a genetic map of the transformation vector pHCE1LB:pgsA-Anal3 31 for surface expression, which uses gram-negative and gram-positive microorganisms as hosts.

*E. coli* was transformed with the transformation vector for surface expression, and the *E. coli* containing the plasmid pHCE1LB:pgsA-Anal3 was deposited under the accession number KCTC 10348BP with the Korean Collection for Type Cultures (KCTC), Korean Research Institute of Bioscience and Biotechnology located at 52 Oun-dong, Yusong, Daejon, Korea.

(2) After *Lactobacillus* was transformed with the transformation vector pHCE1LB:pgsA-Anal3, the presence of the pHCE1LB:pgsA-Anal3 plasmid in the transformed *Lactobacillus* was examined. Also, the expression of the antibiotic peptide Anal3 fused with the pgsA gene was examined.

Figure 7:
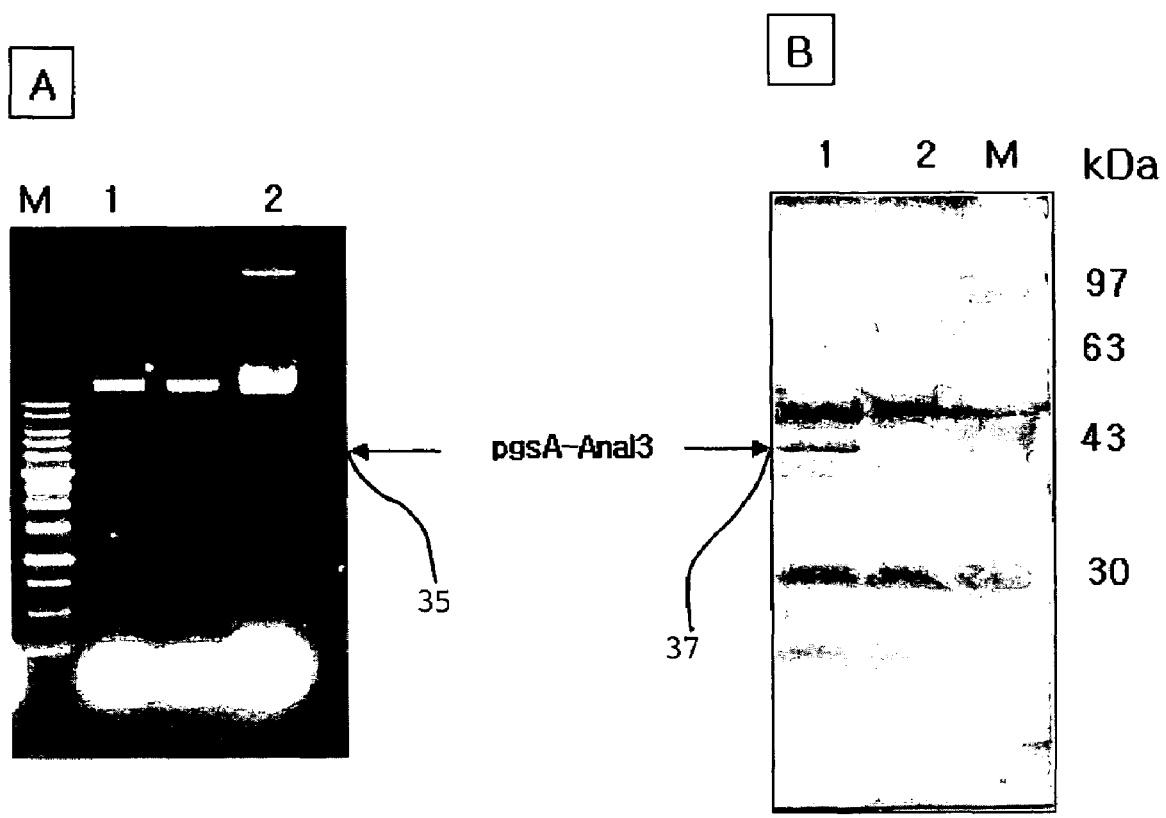
FIG. 7A is a photograph showing a transformation vector plasmid for surface expression separated from lactic acid-forming bacteria transformed with transformation vector pHCE1LB:pgsA-Anal3 for surface expression.
FIG. 7B is a photograph showing the protein expression pattern of peptide antibiotics Anal3 fused with a pgsA gene, in which the protein expression pattern was analyzed by Western blotting analysis with a specific antibody.

For this purpose, *Lactobacillus* was transformed with the expression vector, after which its expression was induced in the same manner as in Example 1. The expression in *Lactobacillus* of the antibiotic peptide Anal3 fused with the C-terminal of the gene pgsA, which is involved in the synthesis of poly-gamma-glutamate, was examined by SDS-polyacrylamide gel electrophoresis (FIG. 7A) and the Western immunoblotting using a specific antibody to the pgsA gene (FIG. 7B). In FIG. 7B, lane 1 represents a transformed pHCE1LB:pgsA-Anal3/*Lactobacillus casei*, and lane 2 represents a non-transformed *Lactobacillus casei*. As shown in FIG. 7B, the fusion protein band of about 44-KDa caused by the pHCE1LB:pgsA-Anal3 plasmid was detected. Since the pgsA gene has about 41.8 KDa and the peptide Anal3 has about 2.2 KDa, it could be found that the 44 KDa band would be a fusion protein where the pgsA gene and the peptide P5 had been fused to each other. FIG. 7A is a photograph showing a transformation vector plasmid for surface expression separated from lactic acid-forming bacteria transformed with transformation vector pHCE1LB: pgsA-Anal3 for surface expression 35, and FIG. 7B is a photograph showing the protein expression pattern of peptide antibiotics Anal3 fused with a pgsA gene 37, in which the protein expression pattern was analyzed by Western blotting analysis with a specific antibody.

EXAMPLE 4

Figure 8:
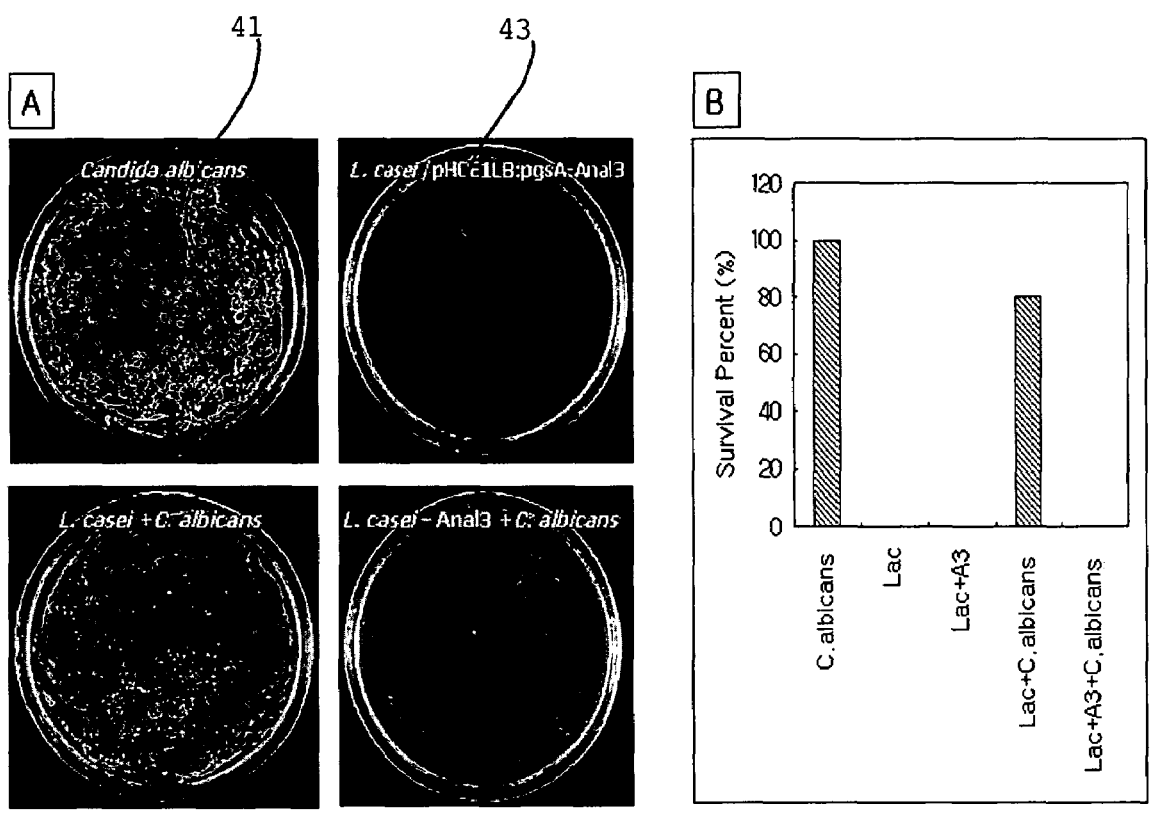
FIG. 8A is a plate photograph showing the antifungal activity against fungus *Candida albicans* of lactic acid-forming bacteria expressing peptide antibiotics Anal3 on their surface.
FIG. 8B is a graphic diagram showing the survival rate of *Candida albicans*.
Figure 9:
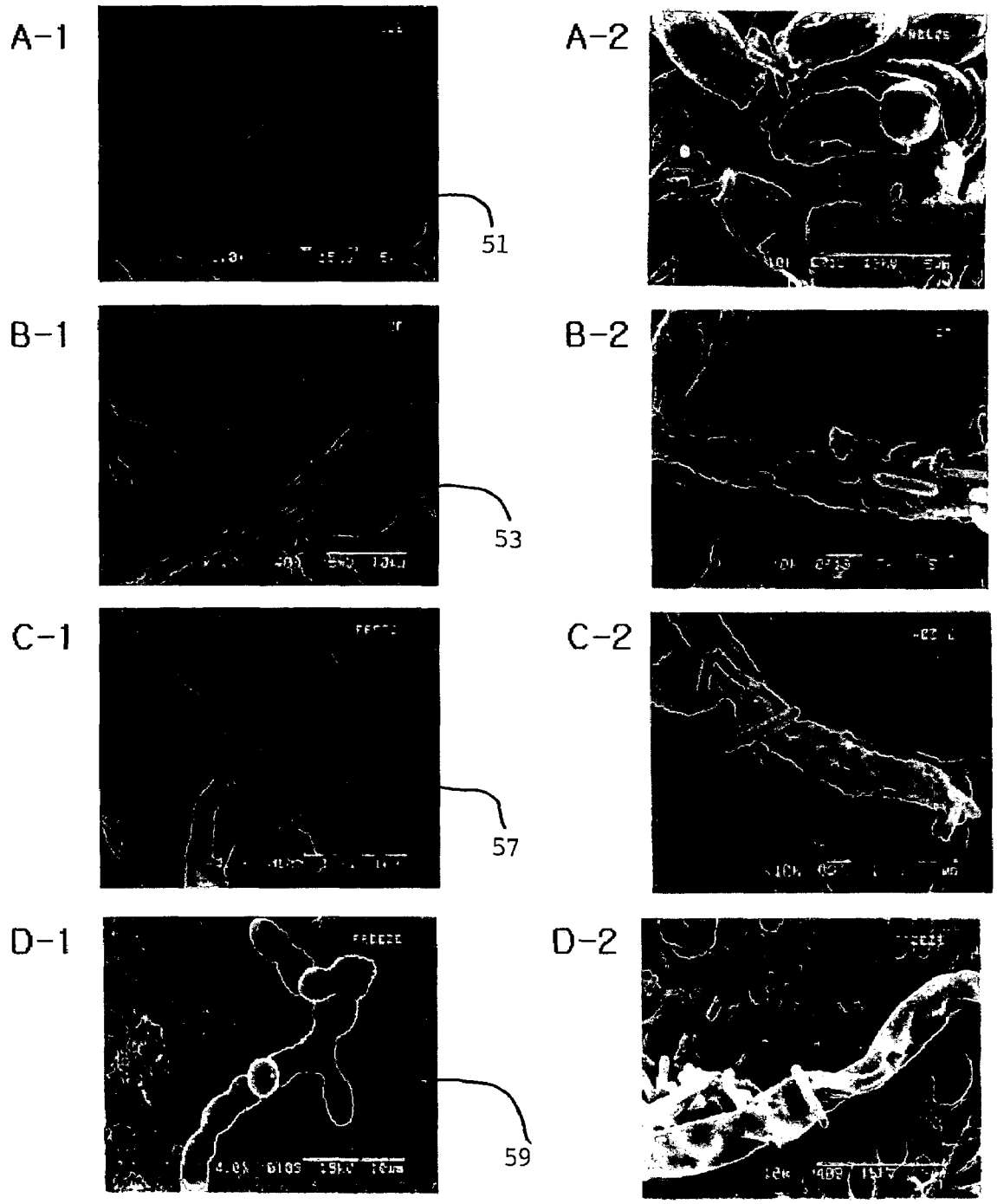
FIGS. 9A to 9D are scanning electron microphotographs showing the antifungal activity against fungi *Candida albicans* (A), *Aspergillus flavus* (B), *Trichosporon beigelli* (C) and *Trichophyton rubrum* (D) of lactic acid-forming bacteria expressing peptide antibiotics Anal3 on their surface.

Measurement of Antifungal Activity of *Lactobacillus* Bacteria Expressing Peptide Antibiotics Anal3 on Their Surface (1) In order to measure the antifungal activity of *Lactobacillus* that had been found in Example 3 to surface-expresses the peptide antibiotics Anal3, a visualization test of antifungal activity was conducted on pathogenic fungus *Candida albicans* 41 (TIMM 1768) in the same manner as in Example 2. As a result, a large number of colonies could be detected on the plates on which the *Candida albicans* strain alone and a mixture of such a strain and wild-type *Lactobacillus* had been plated. However, in the case where the *Lactobacillus* bacteria expressing the peptide antibiotics Anal3 on their surface had been added, it could be found that the growth of the fungi was completely inhibited so that colonies were not detected (FIG. 8A). FIG. 8A is a plate photograph showing the antifungal activity against fungus *Candida albicans* 41 of lactic acid-forming bacteria expressing peptide antibiotics Anal3 on their surface 43, and FIG. 8B is a graphic diagram showing the survival rate of *Candida albicans*. The survival rate of such fungi was graphically shown in FIGS. 8B. Such results indicate that the *Lactobacillus* bacteria expressing the peptide antibiotics P5 on their surface exhibited excellent antifungal activity.

(2) Furthermore, the antifungal activity of the inventive *Lactobacillus* bacteria expressing the peptide antibiotics Anal3 on their surface was examined by SEM on *Candida albicans* 51 (TIMM 1768), *Aspergillus flavus* 53, *Trichosporon beigelii* 55 (KCTC 7707) and *Trichophyton rubrum* 57 in the same manner as in Example 2.

As a result, in the cases where the *Lactobacillus* bacteria expressing the peptide antibiotics Anal3 on their surface had been added to *Candida albicans* (FIG. 9A), *Aspergillus flavus* (FIG. 9B), *Trichosporon beigelii* (FIG. 9C) and *Trichophyton rubrum* (FIG. 9D), it could be found that the cell breakdown of the fungi occurred at a larger amount than the case where the *Lactobacillus* bacteria expressing the peptide antibiotics P5 on their surface had not been added. FIGS. 9A to 9D are scanning electron microphotographs showing the antifungal activity against fungi *Candida albicans* 51 (A), *Aspergillus flavus* 53 (B), *Trichosporon beigelli* 55 (C) and *Trichophyton rubrum* 57 (D) of lactic acid-forming bacteria expressing peptide antibiotics Anal3 on their surface.

EXAMPLE 5

Measurement of Antibacterial Activity Against Other Lactic Acid-forming Bacteria of *Lactobacillus* Bacteria Expressing Peptide Antibiotics P5 and Anal3 on Their Surface In order to measure the antibacterial activity against other lactic acid forming bacteria (*Bifidobacterium longum, Enterococcus faecalis, Lactococcus lactis, Lactobacillus acidophilus, Lactobacillus amylovorus* and *Streptococcus thermophilus*) of the *Lactobacillus* expressing the peptide antibiotics P5 and Anal3, a visualization test was conducted by a paper disc method.

Concretely, $1 \times 10^3$ of each of the strains cultured in MRS medium was plated on a MRS agar plate, and the *Lactobacillus* bacteria expressing the peptide antibiotics P5 and Anal3 on their surface were successively diluted 1/2 times and a paper disc was wet with the dilution. Then, the paper disc (ADVANTEC, Toyo Roshi Kaisha, Japan) was placed on the MRS agar plate on which the lactic acid-forming bacteria had been plated. Then, the paper disc was cultured at 37° C. for one hour, and the rings formed around the paper disc were observed.

Figure 10:
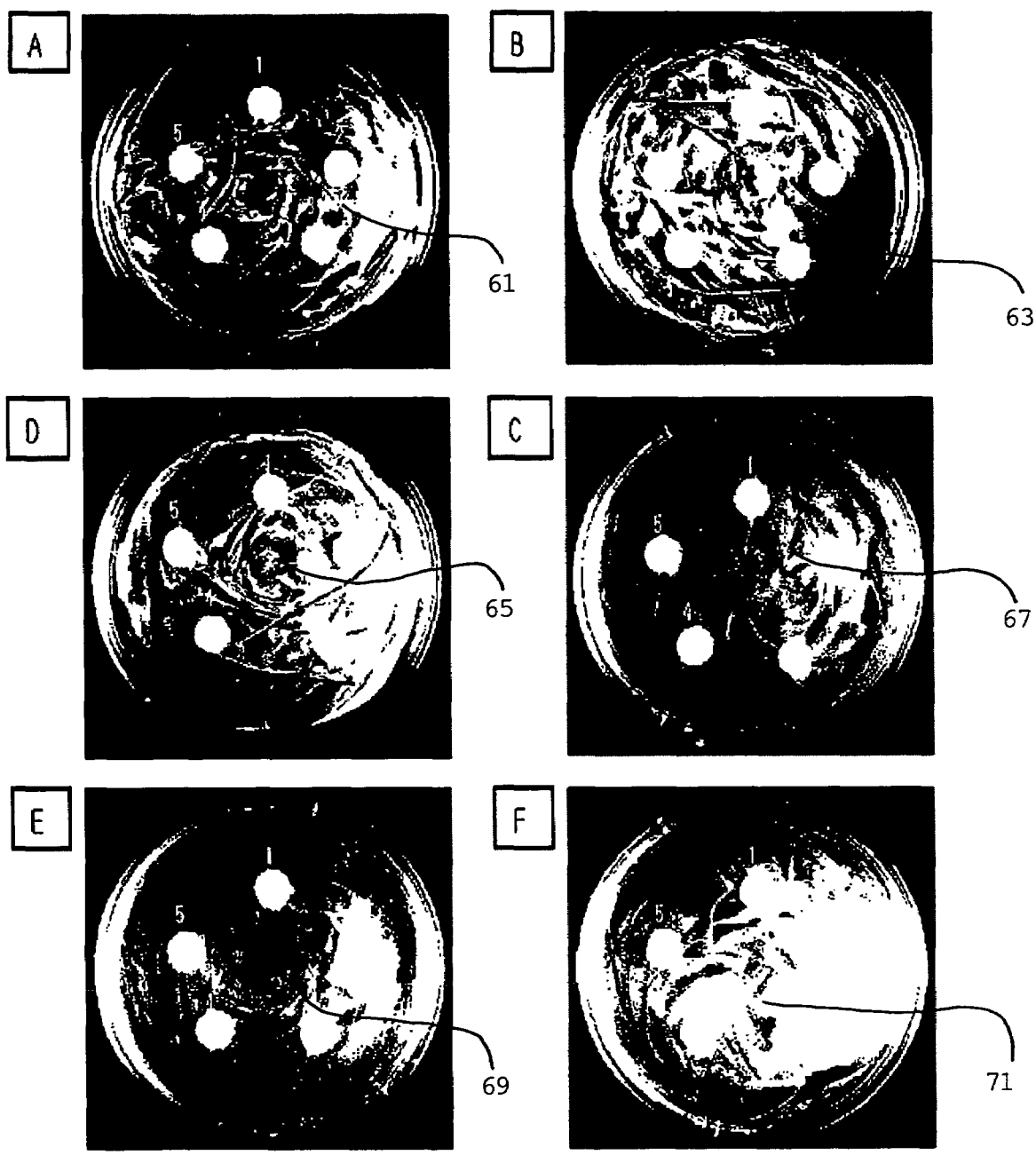
FIGS. 10A to 10F are photographs showing the antibacterial activity against *Bifidobacterium longum* (A), *Enterococcus faecalis* (B), *Lactococcus lactis* (C), *Lactobacillus acidophilus* (D), *Lactobacillus amylovorus* (E) and *Streptococcus thermophilus* (F) of *Lactobacillus* expressing peptide antibiotics P5 and Anal3 on their surface.

The results are shown in FIG. 10. FIGS. 10A to 10F are photographs showing the antibacterial activity against *Bifidobacterium longum* 61 (A), *Enterococcus faecalis* 63 (B), *Lactococcus lactis* 65 (C), *Lactobacillus acidophilus* 67 (D), *Lactobacillus amylovorus* 69 (E) and *Streptococcus thermophilus* 71 (F) of *Lactobacillus* expressing peptide antibiotics P5 and Anal3 on their surface. As shown in FIG. 10, the *Lactobacillus casei* expressing the peptide antibiotics P5 and Anal3 on their surface did not show antibacterial activity against all the tested lactic acid-forming bacteria, including (*Bifidobacterium longum* 61 (FIG. 10A), *Enterococcus faecalis* 63 (FIG. 10B), *Lactococcus lactis* 65 (FIG. 10C), *Lactobacillus acidophilus* 67 (FIG. 10D), *Lactobacillus amylovorus* 69 (FIG. 10E) and *Streptococcus thermophilus* 71 (FIG. 10F). From such results, it could be found that the *Lactobacillus casei* expressing the peptide antibiotics P5 and Anal3 on their surface might be used in combination with lactic bacteria-forming bacteria having other effects.

EXAMPLE 6

Examination Whether Side Effects Caused by Genetic Management is Avoided or Not by Heat-treating of Expressed Peptide Antibiotics and Plasmid With the active development of substances such as genetically managed organisms (GMO), and an increase in their use, the anxiety about the introduction of managed DNAs into other microorganisms, animals and plants, and the induction of various diseases, including cancer, is being increased.

In this Example, therefore, an examination was performed on whether or not the heat-treating of the transformed microorganisms according to the present invention can solve the problems in GMO by maintaining their function as antibiotics while causing damage to genetically managed DNAs (i.e., plasmids).

(1) First, an examination was performed on whether or not the peptide antibiotics are maintained without being degraded, upon their heat-treating.

In the above Examples, it was found that the *Lactobacillus* transformed with each of the expression vectors pHCE1LB:pgsA-P5 and pHCE1LB:pgsA-Anal3 could express the pgsA-fused antibiotic peptide P5 and the pgsA-fused Anal3, respectively.

Figure 11:
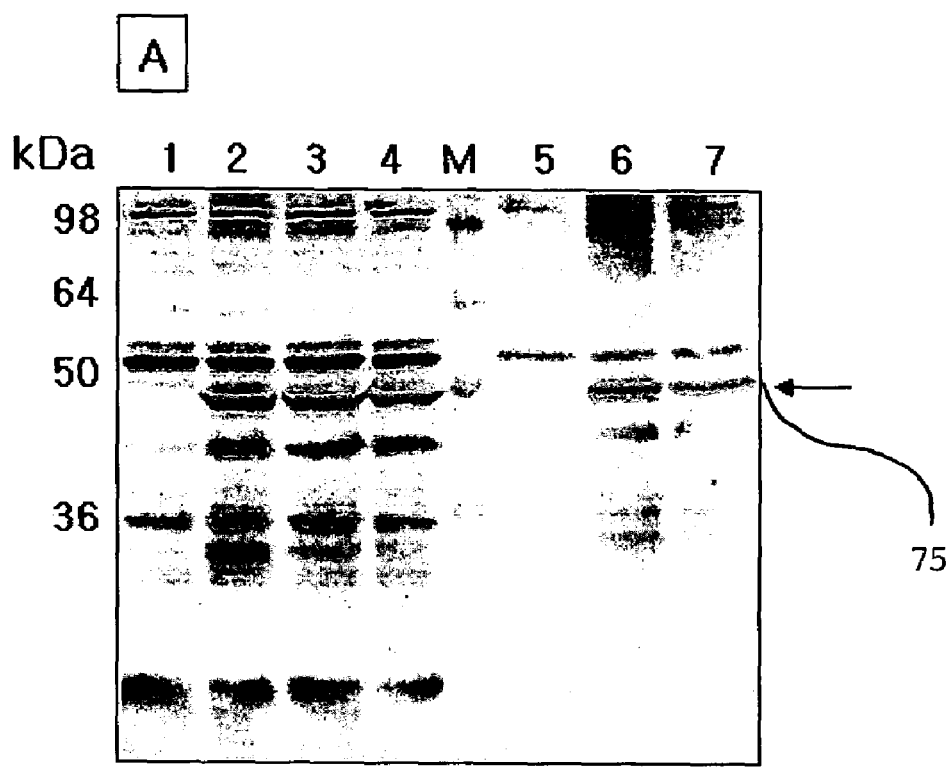
FIG. 11A is a photograph showing that a plasmid is present in *Lactobacillus* after heat-treating the *Lactobacillus* expressing peptide antibiotics P5 and Anal3 on their surface.
FIG. 11B is a photograph showing the condition of peptide antibiotics P5 and Anal3 fusion proteins fused with a pgsA gene.
Figure 11:
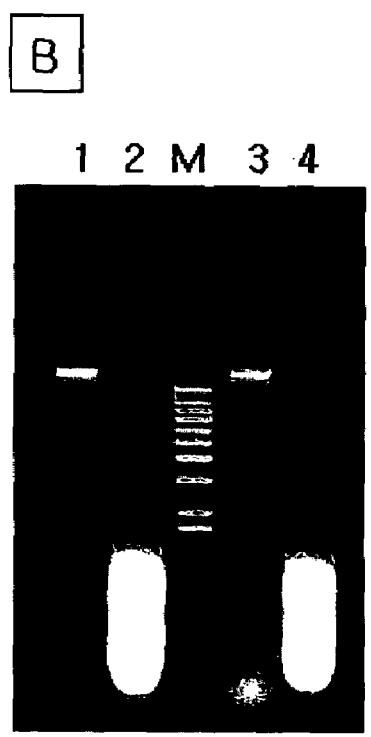

The *Lactobacillus* that had been found to surface-express the fusion proteins by the Western immunoblotting was heat-treated at 110° C. for 20 minutes in the same manner as in Example 1, after which SDS-polyacrylamide gel electrophoresis was performed to examine the conditions of the pgsA-fused peptide antibiotics P5 and the pgsA-fused peptide antibiotics Anal3 (FIG. 11A). FIG. 11A is a photograph showing that a plasmid 75 is present in *Lactobacillus* after heat-treating the *Lactobacillus* expressing peptide antibiotics P5 and Anal3 on their surface, and FIG. 11B is a photograph showing the condition of peptide antibiotics P5 and Anal3 fusion proteins fused with a pgsA gene 77. In FIG. 11A, lane 1 represents a non-transformed viable bacteria *Lactobacillus casei*, lane 2 represents a transformed pHCE1LB:pgsA-P5/viable bacteria *Lactobacillus casei*, lanes 3 and 4 represent a transformed pHCE1LB:pgsA-Anal3/viable bacteria *Lactobacillus casei*, lane 5 represents a non-transformed inactivated (heat-treated) *Lactobacillus casei*, lane 6 represents a transformed pHCE1LB:pgsA-P5/inactivated (heat-treated) bacteria *Lactobacillus casei*, and lane 7 represents a transformed pHCE1LB:pgsA-Anal3/inactivated (heat-treated) bacteria *Lactobacillus caesi*.

As shown in FIG. 11A, it could be found that the pgsA gene and the peptide antibiotics P5 or Anal3 75 were present in the strain in a fusion protein form, similarly to before the strain was heat-treated.

(2) Then, an examination was performed on whether or not the activity of the plasmid in the *Lactobacillus* inactivated by heat-treating was maintained.

As in the above Examples, the *Lactobacillus*, which had been transformed with each of the surface expression vectors pHCE1LB:pgsA-P5 and pHCE1LB:pgsA-Anal3 and found to express the pgsA-fused antibiotic peptide P5 and the pgsA-fused antibiotic peptide Anal3, respectively, was used. The transformed *Lactobacillus* was heat-treated at 110° C. for 20 minutes, and then, the plasmid in the heat-treated *Lactobacillus* was subjected to Western immunoblotting, using a specific antibody to the pgsA gene (FIG. 11B). In FIG. 11B, lane 1 represents a viable bacteria *Lactobacillus casei* transformed with pHCE1LB:pgsA-P5, lane 2 represents an heat-treated *Lactobacillus casei* transformed with pHCE1LB:pgsA-P5, lane 3 represents a viable bacteria *Lactobacillus casei* transformed with pHCE1LB:pgsA-Anal3, and lane 4 represents an inactivated (heat-treated) *Lactobacillus casei* transformed with pHCE1LB:pgsA-Anal3. As shown in FIG. 11B, it could be found that all the plasmids were degraded or denatured by heat-treating.

Although not shown by separate data, when the plasmid, which had been heat-treated in the same manner as described above and then extracted, was transformed into *E. coli*, there was no transformed *E. coli*. Thus, it was found that, when the transformed microorganisms according to the present invention are suitably heat-treated, the migration of the gene through the plasmid or between organisms could be prevented.

INDIRECT EXAMPLES

Construction of Vectors Having Combination of pgsB, pgsC and pgsA Inserted Therein, and Surface Expression Test for Foreign Protein Using the Same It was found that the surface expression vectors, which contain one or more than two genes of the pgsB, pgsC and pgsA encoding the poly-gamma-glutamate synthetase complex, and also a gene encoding a foreign protein other than the peptide antibiotics according to the present invention, could be constructed, and the transformation of microorganisms with such vectors allowed the foreign protein to be expressed on the microbial surface.

This indirectly indicates that the surface expression vectors, which contain one or two or more of the pgsB, pgsC and pgsA genes encoding the poly-gamma-glutamate synthetase complex, and also a gene encoding an amphiphilic peptide with antibacterial, antifungal and anticancer activities, can be constructed and used in surface expression applications.

In the following Indirect Examples, plasmids pGNBCA and pGNC are equal to the plasmids pGNpgsBCA and pGNpgsCA in the present invention, respectively.

INDIRECT EXAMPLE 1

Construction of Transformation Vector pGNBCA-HB168 for Surface Expression, and Surface Expression of Neutralizing Antibody Epitope of S-antigen Using the outer membrane protein genes (pgsBCA), which are derived from *Bacillus* sp. strains and involved in poly-gamma-glutamate, the transformation vector pGN-BCA-HB168 was constructed which can surface-express the neutralizing antibody epitope of a hepatitis B virus S-antigen, using gram-negative microorganisms as hosts.

In order to introduce a hepatitis B virus S-antigen gene into the surface expression vector pGNBCA, PCR using oligonucleotide primers having the base sequences of SEQ ID NO: 8 (5-ctg gga tcc caa ggt atg ttg ccc gtt tg-3) and SEQ ID NO: 9 (5-tga agc tta tta gga cga tgg gat ggg aat-3) was performed using about 1.4-kb hepatitis B virus gene template cloned into general purpose cloning vector pUC8, to amplify an S-antigen gene. The amplified gene site had a 168-bp size.

Figure 12:
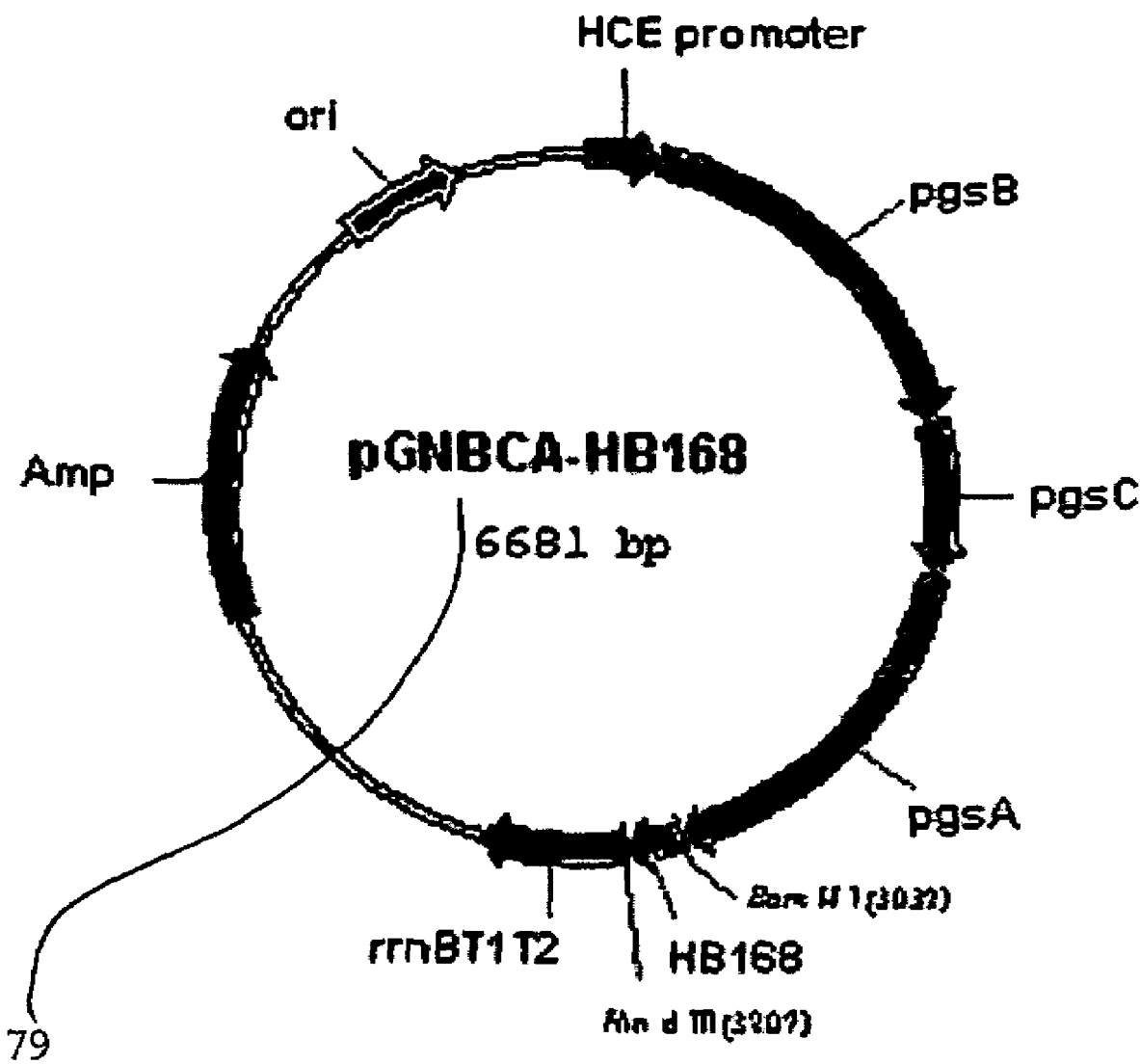
FIG. 12 is the genetic map of surface expression pGNBCA and transformation vector pGNBCA-HB168, which use gram-negative microorganisms as hosts.

The primers of SEQ ID NO: 8 and SEQ ID NO: 9 were so constructed that they have recognition sites for restriction enzymes BamH I and Hind III, which are present in the surface expression vector pGNBCA. The amplified hepatitis B virus S-antigen gene was cut with restriction enzymes BamH I and Hind III, and its translation codon was fitted with the C-terminal of the outer membrane protein gene which is involved in the synthesis of poly-gamma-glutamate. The transformation vector pGNBCA-HB168 79 so produced is shown in FIG. 12. FIG. 12 is the genetic map of surface expression pGNBCA and transformation vector pGNBCA-HB168, which use gram-negative microorganisms as hosts 79.

The transformation vector pGNBCA-HB168 79 for surface expression was used to examine the surface expression in *E. coli* of the neutralizing antibody epitope of the hepatitis B virus S-antigen.

*E. coli* was transformed with the expression vector constructed in Example 2, and then grown in a 500 ml flask including a 50 ml LB medium (5 g/L yeast extract, 10 g/L Tripton, 5 g/L salt, pH 7.0) containing 100 mg/L antibiotics (ampicillin), to induce the surface expression of the peptide antibiotics.

Figure 13:
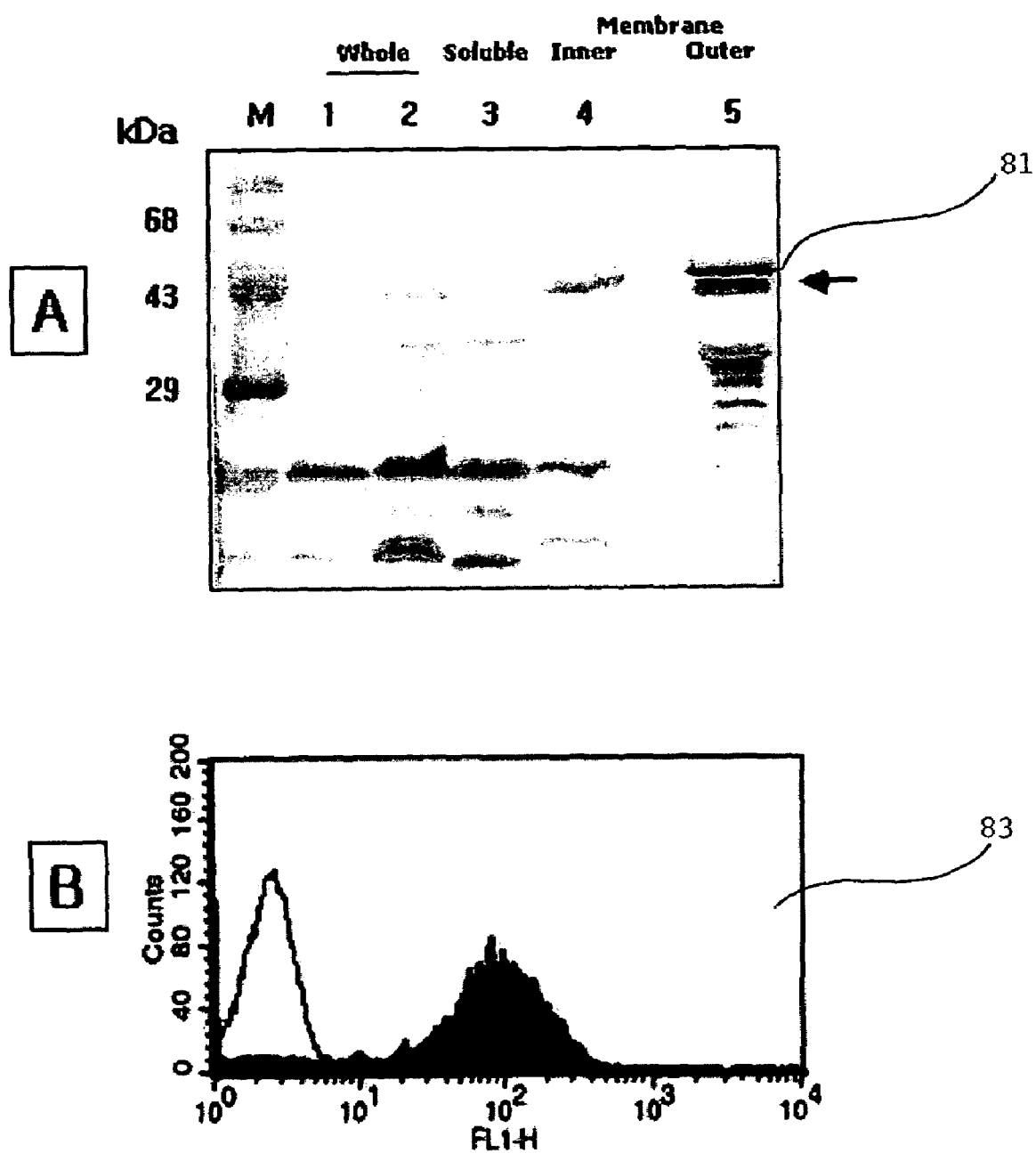
FIG. 13A is a Western blot photograph showing the surface expression of the epitope protein of a hepatitis B virus antigen in the gram-negative microorganism transformed with transformation vector pGNBCA-HB168 for surface expression.
FIG. 13B is a graphic diagram showing the result of fluorescence-activating cell sorting (FACS) flow cytometry.
Figure 14:
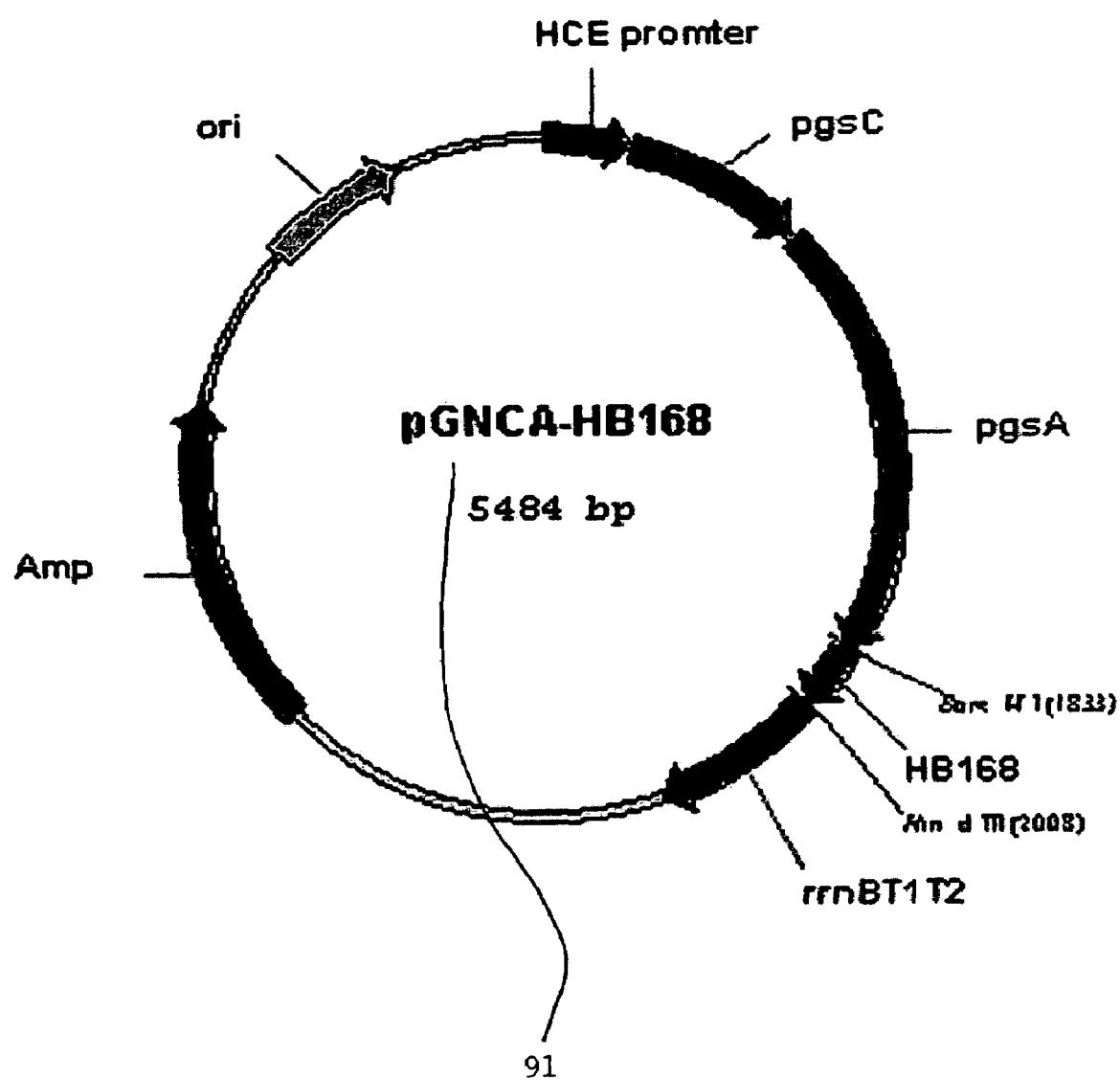
FIG. 14 is the genetic map of surface expression vector pGNCA and transformation vector pGNCA-HB168.
Figure 15:
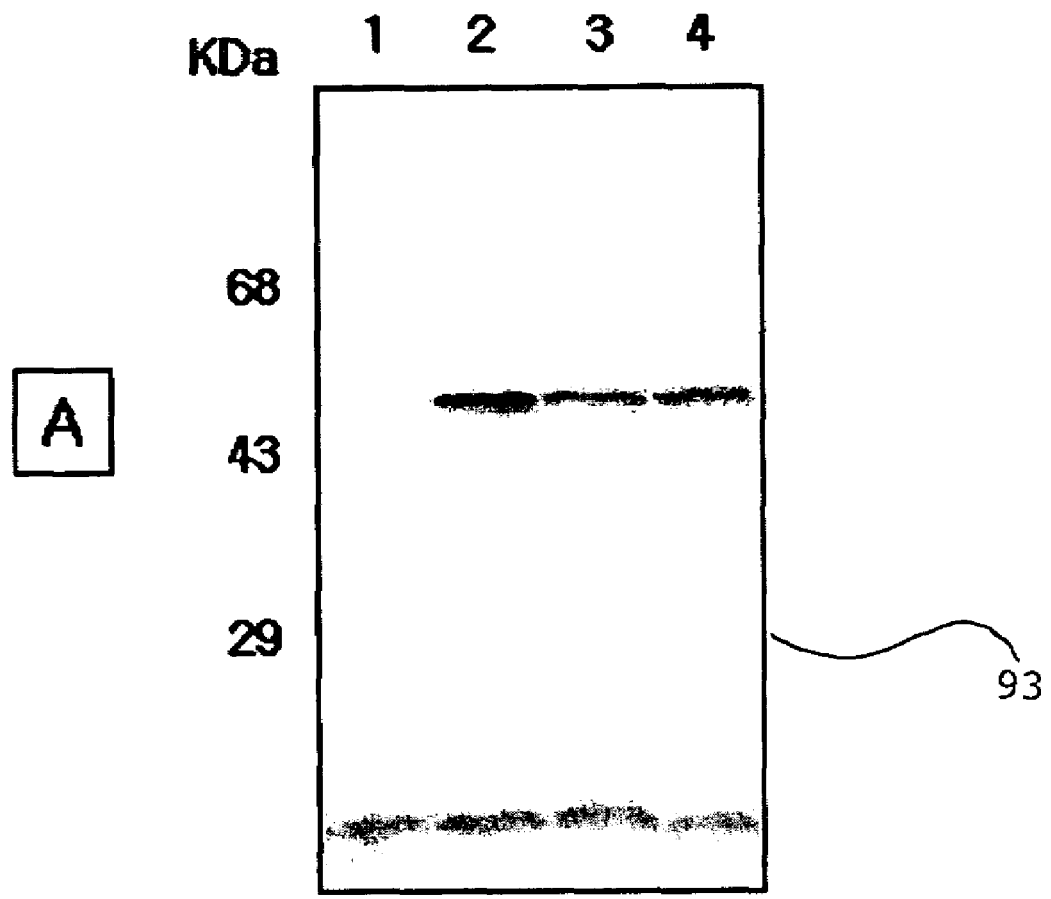
FIG. 15A is a Western blot photograph showing the surface expression of the epitope protein of a hepatitis B virus antigen in the gram-negative microorganism transformed with transformation vector pGNCA-HB168:A2, pGNA-HB168:A3 and pGNHB-A:A4 for surface expression.
FIG. 15B is a graphic diagram showing the result of fluorescence-activating cell sorting (FACS) flow cytometry.
Figure 15:
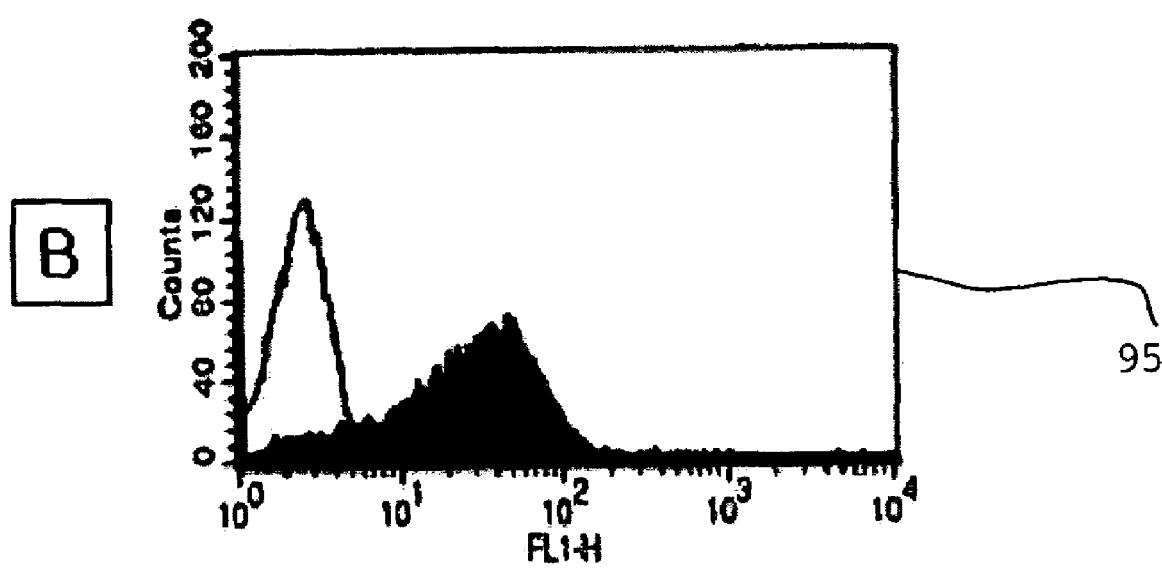

To examine the bacterial expression of the neutralizing antibody-forming epitope of S-antigens fused with the C-terminal of a gene producing poly-gamma-glutamate, SDS-polyacrylamide gel electrophoresis and the Western immunoblotting using a specific antibody to the S antigen were performed. Concretely, a protein obtained at the same cell concentration was denatured to prepare a sample, and the sample was analyzed by SDS-acrylamide gel electrophoresis, and then the protein fractions were transferred to a PVDF membrane. The PDVF membrane to which the protein fractions had been transferred was blocked by shaking in a blocking buffer solution (50 mM Tris HCL, 5% skim milk, pH 8.0) for one hour, and then, polyclonal primary antibody derived from a sheep to the S antigen was 1,000-fold diluted in the blocking buffer solution, and reacted with the membrane for 12 hours. The reacted membrane was washed with buffer solution, and a sheep-derived secondary antibody was 1,000-fold diluted in the blocking buffer solution and reacted with the membrane for 4 hours. After the reaction, the membrane was washed with buffer solution, reacted with an avidin-biotin reagent for 1 hour and washed again. The washed membrane was developed by the addition of $H_2O_2$ as a substrate and DAB solution as a color development reagent, and the specific binding between the specific antibody to the S-antigen and the fusion protein was examined (FIG. 13A). In FIG. 13A, lane 1 represents a JM109 whole cell as a non-transformed host cell, and lane 2 represents the whole cell of transformed pGNBCA-HB168/JM109. FIG. 13A is a Western blot photograph showing the surface expression of the epitope protein of a hepatitis B virus antigen in the gram-negative microorganism transformed with transformation vector pGNBCA-HB168 for surface expression 81, and FIG. 13B is a graphic diagram showing the result of fluorescence-activating cell sorting (FACS) flow cytometry 83.

Also, in order to directly confirm that the neutralizing antibody-forming epitope is expressed on the surface of *E. coli*, each of the soluble fraction, inner membrane and outer membrane fractions of *E. coli* whose expression had been induced by outer membrane fractionation was separated. Then, the separated fraction was subjected to SDS-polyamideacrylamide gel electrophoresis and the Western blotting using a specific antibody to the S-antigen. The results are shown in FIG. 13A. In FIG. 13A, lane 3 represents the soluble fraction of transformed pGNBCA-HB168/JM109, lane 4 represents the inner membrane fraction of transformed pGNBCA-HB168/JM109, and lane 5 represents the outer membrane faction of transformed pGNBCA-HB168/JM109. As shown in FIG. 13A, it could be found that the neutralizing antibody epitope of the S-antigen was located at the outer membrane, and the fusion protein band of about 48-KDa caused by the pGNBCA-HB168 plasmid 81 was detected.

The fact that the neutralizing antibody epitope of the S-antigen is expressed on the surface of *E. coli* by the C-terminal of a poly-gamma-glutamate synthetase protein was examined by fluorescence-activating cell sorting (FACS) flow cytometry. For immunofluorescent staining, *E. coli* whose expression had been induced was collected at the same cell concentration. Next, the resulting cells were washed with PBS buffer (pH 7.4) several times, and suspended in 1 ml buffer solution containing 1% bovine serum albumin. A polyclonal primary antibody derived from a sheep was 1,000-fold diluted in the suspension, and reacted with the cells at 4° C. for 12 hours. After the reaction, the cells were washed several times with 1 ml buffer solution, suspended in 1% bovine serum albumin. Then, a biotin-bound secondary antibody was 1,000-fold diluted in the suspension and reacted with the cells at 4° C. for 3 hours. After the reaction, the cells were washed several times with buffer solution, and suspended in 0.1 ml buffer solution containing 1% bovine serum albumin. Then, a streptavidin-R-phycoerythrin specific to biotin was 1,000-fold diluted in the suspension and bound to the cells.

After the reaction, the *E. coli* was washed several times, and subjected to fluorescence-activating cell sorting (FACS) flow cytometry. The results showed that the neutralizing antibody epitope of the S-antigen, which is compared to non-transformed *E. coli*, was expressed on the surface of the *E. coli* (FIG. 13B). In FIG. 13B, white color represents the cells derived from non-transformed JM109, and black color represents the cells derived from transformed pGNBCA-HB168/JM109. As shown 83 in FIG. 13B, it was found that, in the non-transformed *E. coli*, the neutralizing antibody epitope of the S-antigen was not expressed, but in the *E. coli* transformed with the surface expression vector, the neutralizing antibody epitope of the S-antigen was expressed.

INDIRECT EXAMPLE 2

Production of Transformation Vector pGNCA-HB168 for Surface Expressions and Surface Expression of Neutralizing Antibody Epitope of Hepatitis B Virus S-antigen Using the pgsC and pgsA genes among the outer membrane protein genes pgsBCA, which are derived from *Bacillus* sp. strains and involved in the synthesis of poly-gamma-glutamate, the surface expression vectors using gram-negative microorganisms as hosts were constructed.

In order to obtain genes encoding the N- and C-terminals of the pgsC and pgsA proteins among outer membrane proteins that are involved in the synthesis of poly-gamma-glutamate, PCR using the total chromosome as a template, and an oligonucleotide primer having the base sequence of SEQ ID NO: 10 (5'-gca cat atg ttc gga tca gat tta tac atc-3') at the N-terminal, and the base sequence of SEQ ID NO: 11 (5'-ctc gga tcc ttt aga ttt tag ttt gtc act-3') at the C-terminal, was performed.

The N-terminal primer with the base sequence of SEQ ID NO: 10 was so constructed that it has a recognition site for the restriction enzyme Nde I present in expression vector pHCE 19T(II). The amplified gene had about 1.6-bp size from the N-terminal to the C-terminal of the outer membrane protein pgsC that is involved in the synthesis of poly-gamma-glutamate.

The gene amplified by PCR was cut with restriction enzymes Nde I and BamH I, and inserted into the vector pHCE 19T(II) for high-level constitutive expression that had been cut with Nde I and BamH I. This gives a new vector with about 5.3-bp size, which has no translation termination codon at the outer membrane protein involving in the synthesis of poly-gamma-glutamate, and contains new recognition sites for restriction enzymes. This vector was termed pGNCA.

Using the pgsC and pgsA genes among the outer membrane proteins pgsBCA that are involved in the synthesis of poly-gamma-glutamate, the transformation vector pGNCA-HB168, which can surface-express the neutralizing antibody epitope of the hepatitis B virus S-antigen, using gram-negative microorganisms as hosts, was constructed in the same manner as in Example 2. The transformation vector pGNCA-HB168 91 so produced is shown in FIG. 14. FIG. 14 is the genetic map of surface expression vector pGNCA and transformation vector pGNCA-HB168 91.

The surface expression vector pGNCA-HB168 91 was used to examine the expression in *E. coli* of the neutralizing antibody epitope of the hepatitis B virus S-antigen.

For this, *E. coli* was transformed with the surface expression vector, and its expression was induced in the same manner as in Example 3. Then, to confirm that the neutralizing antibody epitope of the S-antigen, which had been fused with the outer membrane proteins pgsCA, was expressed in *E. coli*, SDS-polyacrylamide gel electrophoresis and the Western immunoblotting using a specific antibody to the S-antigen were performed 93. The results are shown in FIG. 15A. FIG. 15B is a graphic diagram 95 showing the result of fluorescence-activating cell sorting (FACS) flow cytometry. FIG. 15A is a Western blot photograph 93 showing the surface expression of the epitope protein of a hepatitis B virus antigen in the gram-negative microorganism transformed with transformation vector pGNCA-HB168:A2, pGNA-HB168:A3 and pGNHB-A:A4 for surface expression, and FIG. 15B is a graphic diagram showing the result of fluorescence-activating cell sorting (FACS) flow cytometry.

In FIG. 15A, lane 1 represents non-transformed host cell JM109, lane 2 represents a transformed pGNCA-HB168/JM109, lane 3 represents a transformed pGNA-HB168/JM109, and lane 4 represents a transformed pGNHB168-pgsA/JM 109. As shown in FIG. 15A, the fusion protein band of about 48 KDa by the pGNCA-HB168 plasmid could be detected. FIG. 15B is a graphic diagram showing the result of fluorescence-activating cell sorting (FACS) flow cytometry. In FIG. 15B, white color represents the cells derived from the non-transformed JM109, and black color represents the cells derived from a transformed pGNCA-HB168/JM109. As shown in FIG. 15B, it could be found that, in the non-transformed *E. coli*, the neutralizing antibody epitope of the S-antigen was not expressed, but in the transformed *E. coli*, the neutralizing antibody epitope of the S-antigen was expressed on the surface of the *E. coli.*

As described and proved in detail above, according to the present invention, the surface expression vectors capable of expressing the amphiphilic peptide antibiotics P5 and Anal3 with antibacterial, antifungal and antibacterial activities on the cell surface are provided using all or parts of the outer membrane genes pgsBCA, as surface expression motifs, which are derived from *Bacillus* sp. strains and involved in the synthesis of poly-gamma-glutamate. Such surface expression vectors can effectively express a foreign protein on the cell surface.

According to the present invention, the peptide antibiotics can be expressed on the surface of various microorganisms transformed with the surface expression vectors. The surface expression method for the peptide antibiotics according to the present invention allows the peptide antibiotics to be mass-produced without a purification process. Particularly, the inventive method utilizes lactic acid-forming bacteria themselves, which are harmless to the human body and have the effects demonstrated in the pharmaceutical and food fields, so that it can provide the peptide antibiotics at low prices and large amounts. Thus, the inventive method has very high industrial applicability.

While the present invention has been described with reference to the particular illustrative embodiment, it is not to be restricted by the embodiment but only by the appended claims. It is to be appreciated that those skilled in the art can change or modify the embodiment without departing from the scope and spirit of the present invention.

INDUSTRIAL APPLICABILITY

The invention has industrial applicability in the pharmaceutical field.

SEQUENCE LISTING

Please see attached paper copy of computer readable form of sequence listing.

What is claimed is:

1. A vector for the surface expression of antibiotics, which comprises:
   one or more than two genes selected from the group consisting of pgsB, pgsC and pgsA, said genes encoding a poly-gamma-glutamate synthetase complex; and
   a gene encoding P5 peptide having antibacterial, antifungal and anticancer activities fused with said gene encoding a poly-gamma-glutamate synthetase complex, wherein P5 peptide is encoded by the base sequence of SEQ ID NO: 4.

2. The vector according to claim 1, wherein said pgsB, pgsC and pgsA genes have the base sequences described in SEQ ID NO: 1, SEQ ID NO: 2 and SEQ ID NO: 3, respectively.

3. The vector according to claim 1, wherein the vector contains the pgsA gene among the genes encoding the poly-gamma-glutamate synthetase complex.

4. The vector according to claim 1, said vector is pHCE1LB:pgsA-P5 for the surface expression of antibiotics, which expresses said antibiotic on the surface of gram-negative and gram positive bacteria.

5. A microorganism transformed with the vector of claim 1.

6. *E. Coli* (KCTC 10350BP) transformed with the vector pHCE1LB:pgsA-P5 of claim 4.

7. A lactic acid-forming bacteria transformed with the vector of claim 1.

8. A pharmaceutical composition and suspension of the same for antibacterial, antifungal or anticancer application, which comprises, as an active ingredient, the lactic acid-forming bacteria according to claim 7 and having the peptide antibiotic P5 expressed on their surface.

9. The pharmaceutical composition according to claim 8, wherein said active ingredient is heat-treated.

* * * * *